(12) United States Patent
Tetzlaff et al.

(10) Patent No.: US 7,582,087 B2
(45) Date of Patent: Sep. 1, 2009

(54) VESSEL SEALING INSTRUMENT

(75) Inventors: Philip M. Tetzlaff, Superior, CO (US);
Carolyn H. Mihaichuk, Erie, CO (US);
Duane E. Kerr, Berthoud, CO (US);
Dave A. Schechter, Boulder, CO (US);
Jon Sherman, Cincinnati, OH (US); Ted Richardson, Cincinnati, OH (US); Greg Drach, Liberty Township, OH (US)

(73) Assignee: Covidien AG, Neuhausen am Rheinfall (CH)

( * ) Notice: Subject to any disclaimer, the term of this patent is extended or adjusted under 35 U.S.C. 154(b) by 250 days.

(21) Appl. No.: 10/474,170

(22) PCT Filed: Apr. 6, 2001

(86) PCT No.: PCT/US01/11420

§ 371 (c)(1),
(2), (4) Date: Mar. 10, 2004

(87) PCT Pub. No.: WO02/080797

PCT Pub. Date: Oct. 17, 2002

(65) Prior Publication Data

US 2004/0162557 A1 Aug. 19, 2004

Related U.S. Application Data

(63) Continuation-in-part of application No. 09/425,696, filed on Oct. 22, 1999, now Pat. No. 6,511,480, which is a continuation-in-part of application No. 09/178,027, filed on Oct. 23, 1998, now Pat. No. 6,277,117.

(51) Int. Cl.
*A61B 18/14* (2006.01)

(52) U.S. Cl. .......................... 606/51; 606/52

(58) Field of Classification Search .................. 606/41, 606/45, 46, 47, 48, 49–52, 205–208
See application file for complete search history.

(56) References Cited

U.S. PATENT DOCUMENTS 371,664 A 10/1887 Brannan et al.

(Continued)

FOREIGN PATENT DOCUMENTS

CA 2104423 2/1994

(Continued)

OTHER PUBLICATIONS

Int'l Search Report EP 05013463.4 dated Sep. 28, 2005.

(Continued)

*Primary Examiner*—Lee S Cohen

(57) ABSTRACT

A bipolar electrosurgical instrument for clamping, grasping, manipulating, and sealing tissue includes first and second shafts each having a jaw member extending from a distal end thereof and a handle disposed at a proximal end thereof. The handle being operable to effect movement of the jaw members relative to one another from a first position wherein the jaw members are disposed in spaced relation relative to one another to a second position wherein the jaw members cooperate to grasp tissue therebetween. The bipolar instrument is connectable to a source of electrical energy having a first electrical potential connected to one of the jaw members and a second electrical potential connected to the other of the jaw members such that the jaw members are capable of selectively conducting energy through tissue held therebetween to effect a seal. Both the first and second electrical potentials are transmitted to the jaw members through the first shaft.

16 Claims, 7 Drawing Sheets

U.S. PATENT DOCUMENTS

| | | |
|---|---|---|
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,176,479 A | 10/1939 | Willis |
| 2,279,753 A | 4/1942 | Knopp |
| 2,305,156 A | 12/1942 | Grubel |
| 2,632,661 A | 3/1953 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,720,896 A | 3/1973 | Beierlein |
| 3,763,726 A | 10/1973 | Hildebrand |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,233,734 A | 11/1980 | Bies |
| 4,300,564 A | 11/1981 | Furihata |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Koch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,846,171 A | 7/1989 | Kauphusman et al. |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,035,695 A | 7/1991 | Weber, Jr. et al. |
| 5,084,057 A | 1/1992 | Green et al. |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Xamiyama et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,314,445 A | 5/1994 | Degwitz et al. |
| 5,318,589 A | 6/1994 | Lichtman |
| 5,324,289 A | 6/1994 | Eggers |
| 5,326,806 A | 7/1994 | Yokoshima et al. |
| 5,330,471 A | 7/1994 | Eggers |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,376,089 A | 12/1994 | Smith |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |

| | | | | | |
|---|---|---|---|---|---|
| 5,462,546 A | 10/1995 | Rydell | 5,772,670 A | 6/1998 | Brosa |
| 5,472,443 A | 12/1995 | Cordis et al. | 5,776,128 A | 7/1998 | Eggers |
| 5,478,351 A | 12/1995 | Meade et al. | 5,776,130 A | 7/1998 | Buysse et al. |
| 5,480,409 A | 1/1996 | Riza | 5,779,701 A | 7/1998 | McBrayer et al. |
| 5,484,436 A | 1/1996 | Eggers et al. | H1745 H | 8/1998 | Paraschac |
| 5,496,312 A | 3/1996 | Klicek | 5,792,137 A | 8/1998 | Carr et al. |
| 5,496,317 A | 3/1996 | Goble et al. | 5,792,177 A | 8/1998 | Kaseda |
| 5,496,347 A | 3/1996 | Hashiguchi et al. | 5,797,927 A | 8/1998 | Yoon |
| 5,499,997 A | 3/1996 | Sharpe et al. | 5,797,938 A | 8/1998 | Paraschac et al. |
| 5,509,922 A | 4/1996 | Aranyi et al. | 5,797,941 A | 8/1998 | Schulze et al. |
| 5,514,134 A | 5/1996 | Rydell et al. | 5,797,958 A | 8/1998 | Yoon |
| 5,527,313 A | 6/1996 | Scott et al. | 5,800,449 A | 9/1998 | Wales |
| 5,531,744 A | 7/1996 | Nardella et al. | 5,807,393 A | 9/1998 | Williamsom, IV et al. |
| 5,536,251 A | 7/1996 | Evard et al. | 5,810,808 A | 9/1998 | Eggers |
| 5,540,684 A | 7/1996 | Hassler, Jr. | 5,810,811 A | 9/1998 | Yates et al. |
| 5,540,685 A | 7/1996 | Parins et al. | 5,810,877 A | 9/1998 | Roth et al. |
| 5,540,715 A | 7/1996 | Katsaros et al. | 5,814,043 A | 9/1998 | Shapeton |
| 5,542,945 A | 8/1996 | Fritzsch | 5,820,630 A | 10/1998 | Lind |
| 5,558,671 A | 9/1996 | Yates | 5,827,271 A | 10/1998 | Buysse et al. |
| 5,558,672 A | 9/1996 | Edwards et al. | 5,827,279 A | 10/1998 | Hughett et al. |
| 5,562,699 A | 10/1996 | Heimberger et al. | 5,827,281 A | 10/1998 | Levin |
| 5,569,241 A | 10/1996 | Edwardds | 5,827,323 A | 10/1998 | Klieman et al. |
| 5,569,243 A | 10/1996 | Kortenbach et al. | 5,827,548 A | 10/1998 | Lavallee et al. |
| 5,571,100 A | 11/1996 | Goble et al. | 5,833,690 A | 11/1998 | Yates et al. |
| 5,573,424 A | 11/1996 | Poppe | 5,843,080 A | 12/1998 | Fleenor et al. |
| 5,573,534 A | 11/1996 | Stone | 5,849,022 A | 12/1998 | Sakashita et al. |
| 5,573,535 A | 11/1996 | Viklund | 5,853,412 A | 12/1998 | Mayenberger |
| 5,575,805 A | 11/1996 | Li | 5,860,976 A | 1/1999 | Billings et al. |
| 5,578,052 A | 11/1996 | Koros et al. | 5,876,401 A | 3/1999 | Schulze et al. |
| 5,582,611 A | 12/1996 | Tsuruta et al. | 5,882,567 A | 3/1999 | Cavallaro et al. |
| 5,585,896 A | 12/1996 | Yamazaki et al. | 5,891,141 A | 4/1999 | Rydell |
| 5,590,570 A | 1/1997 | LeMaire, III et al. | 5,891,142 A | 4/1999 | Eggers et al. |
| 5,597,107 A | 1/1997 | Knodel et al. | 5,893,863 A | 4/1999 | Yoon |
| 5,601,601 A | 2/1997 | Tal et al. | 5,893,875 A | 4/1999 | O'Connor et al. |
| 5,603,711 A | 2/1997 | Parins et al. | 5,893,877 A | 4/1999 | Gampp, Jr. et al. |
| 5,603,723 A | 2/1997 | Aranyi et al. | 5,902,301 A | 5/1999 | Olig |
| 5,611,798 A | 3/1997 | Eggers | 5,906,630 A | 5/1999 | Anderhub et al. |
| 5,620,453 A | 4/1997 | Nallakrishnan | 5,908,420 A | 6/1999 | Parins et al. |
| 5,624,452 A | 4/1997 | Yates | 5,908,432 A | 6/1999 | Pan |
| 5,626,578 A | 5/1997 | Tihon | 5,911,719 A | 6/1999 | Eggers |
| 5,626,609 A | 5/1997 | Zvenyatsky et al. | 5,913,874 A | 6/1999 | Berns et al. |
| 5,630,833 A | 5/1997 | Katsaros et al. | 5,921,984 A | 7/1999 | Sutcu et al. |
| 5,637,110 A | 6/1997 | Pennybacker et al. | 5,925,043 A | 7/1999 | Kumar et al. |
| 5,638,003 A | 6/1997 | Hall | 5,935,126 A | 8/1999 | Riza |
| 5,643,294 A | 7/1997 | Tovey et al. | 5,944,718 A | 8/1999 | Austin et al. |
| 5,647,869 A | 7/1997 | Goble et al. | 5,951,549 A | 9/1999 | Richardson et al. |
| 5,647,871 A | 7/1997 | Levine et al. | 5,954,720 A | 9/1999 | Wilson et al. |
| 5,649,959 A | 7/1997 | Hannam et al. | 5,957,923 A | 9/1999 | Hahnen et al. |
| 5,658,281 A | 8/1997 | Heard | 5,960,544 A | 10/1999 | Beyers |
| 5,662,667 A | 9/1997 | Knodel | 5,961,514 A | 10/1999 | Long et al. |
| 5,665,100 A | 9/1997 | Yoon | 5,964,758 A | 10/1999 | Dresden |
| 5,667,526 A | 9/1997 | Levin | 5,976,132 A | 11/1999 | Morris |
| 5,674,220 A | 10/1997 | Fox et al. | 5,984,939 A | 11/1999 | Yoon |
| 5,681,282 A | 10/1997 | Eggers et al. | 5,989,277 A | 11/1999 | LeMaire, III et al. |
| 5,688,270 A | 11/1997 | Yates et al. | 5,997,565 A | 12/1999 | Inoue |
| 5,693,051 A | 12/1997 | Schulze et al. | 6,004,335 A | 12/1999 | Vaitekunas et al. |
| 5,695,522 A | 12/1997 | LeMaire, III et al. | 6,010,516 A | 1/2000 | Hulka et al. |
| 5,700,261 A | 12/1997 | Brinkerhoff | 6,024,741 A | 2/2000 | Williamson et al. |
| 5,702,390 A | 12/1997 | Austin et al. | 6,024,744 A | 2/2000 | Kese et al. |
| 5,707,369 A | 1/1998 | Vaitekunas et al. | 6,030,384 A | 2/2000 | Nezhat |
| 5,709,680 A | 1/1998 | Yates et al. | 6,033,399 A | 3/2000 | Gines |
| 5,716,366 A | 2/1998 | Yates | 6,039,733 A | 3/2000 | Buysse et al. |
| 5,722,421 A | 3/1998 | Francese et al. | 6,041,679 A | 3/2000 | Slater et al. |
| 5,725,536 A | 3/1998 | Oberlin et al. | 6,050,996 A | 4/2000 | Schmaltz et al. |
| 5,727,428 A | 3/1998 | LeMaire, III et al. | 6,053,914 A | 4/2000 | Eggers et al. |
| 5,735,848 A | 4/1998 | Yates et al. | 6,053,933 A | 4/2000 | Balazs et al. |
| 5,743,906 A | 4/1998 | Parins et al. | D424,694 S | 5/2000 | Tetzlaff et al. |
| 5,755,717 A | 5/1998 | Yates et al. | D425,201 S | 5/2000 | Tetzlaff et al. |
| 5,766,130 A | 6/1998 | Selmonosky | 6,059,782 A | 5/2000 | Novak et al. |
| 5,766,166 A | 6/1998 | Hooven | 6,074,386 A | 6/2000 | Goble et al. |
| 5,766,170 A | 6/1998 | Eggers | RE36,795 E | 7/2000 | Rydell |
| 5,769,849 A | 6/1998 | Eggers | 6,083,223 A | 7/2000 | Baker |
| 5,772,655 A | 6/1998 | Bauer et al. | 6,086,586 A | 7/2000 | Hooven |

| | | | | | | |
|---|---|---|---|---|---|---|
| 6,090,107 | A | 7/2000 | Borgmeier et al. | 6,562,037 | B2 | 5/2003 | Paton et al. |
| 6,096,031 | A | 8/2000 | Mitchell et al. | 6,569,162 | B2 | 5/2003 | He |
| 6,096,037 | A | 8/2000 | Mulier et al. | 6,585,735 | B1 | 7/2003 | Frazier et al. |
| 6,099,550 | A | 8/2000 | Yoon | 6,616,658 | B2 | 9/2003 | Ineson |
| 6,102,909 | A | 8/2000 | Chen et al. | 6,616,661 | B2 | 9/2003 | Wellman et al. |
| 6,110,171 | A | 8/2000 | Rydell | 6,620,161 | B2 | 9/2003 | Schulze et al. |
| 6,113,596 | A | 9/2000 | Hooven et al. | 6,641,595 | B1 | 11/2003 | Moran et al. |
| 6,113,598 | A | 9/2000 | Baker | 6,652,514 | B2 | 11/2003 | Ellman et al. |
| 6,117,158 | A | 9/2000 | Measamer et al. | 6,652,521 | B2 | 11/2003 | Schulze |
| 6,123,701 | A | 9/2000 | Nezhat | 6,656,177 | B2 | 12/2003 | Truckai et al. |
| H1904 | H | 10/2000 | Yates et al. | 6,669,696 | B2 | 12/2003 | Bacher et al. |
| 6,126,658 | A | 10/2000 | Baker | 6,676,660 | B2 | 1/2004 | Wampler et al. |
| 6,152,923 | A | 11/2000 | Ryan | 6,679,882 | B1 | 1/2004 | Kornerup |
| 6,162,220 | A | 12/2000 | Nezhat | 6,682,528 | B2 | 1/2004 | Frazier et al. |
| 6,174,309 | B1 | 1/2001 | Wrublewski et al. | 6,685,724 | B1 | 2/2004 | Haluck |
| 6,179,834 | B1 | 1/2001 | Buysse et al. | 6,689,131 | B2 | 2/2004 | McClurken |
| 6,179,837 | B1 | 1/2001 | Hooven | 6,692,445 | B2 | 2/2004 | Roberts et al. |
| 6,183,467 | B1 | 2/2001 | Shapeton et al. | 6,702,810 | B2 | 3/2004 | McClurken et al. |
| 6,187,003 | B1 | 2/2001 | Buysse et al. | 6,726,068 | B2 | 4/2004 | Miller |
| 6,190,386 | B1 | 2/2001 | Rydell | 6,733,498 | B2 | 5/2004 | Paton et al. |
| 6,193,718 | B1 | 2/2001 | Kortenbach et al. | 6,736,813 | B2 | 5/2004 | Yamauchi et al. |
| 6,206,876 | B1 | 3/2001 | Levine et al. | 6,743,229 | B2 | 6/2004 | Buysse et al. |
| 6,206,877 | B1 | 3/2001 | Kese et al. | 6,743,230 | B2 | 6/2004 | Lutze et al. |
| 6,217,602 | B1 | 4/2001 | Redmon | 6,757,977 | B2 | 7/2004 | Dambal et al. |
| 6,221,039 | B1 | 4/2001 | Durgin et al. | 6,770,072 | B1 | 8/2004 | Truckai et al. |
| 6,224,593 | B1 | 5/2001 | Ryan et al. | 6,773,409 | B2 | 8/2004 | Truckai et al. |
| 6,228,080 | B1 | 5/2001 | Gines | 6,773,434 | B2 | 8/2004 | Ciarrocca |
| 6,228,083 | B1 | 5/2001 | Lands et al. | 6,775,575 | B2 | 8/2004 | Bommannan et al. |
| 6,267,761 | B1 | 7/2001 | Ryan | 6,776,780 | B2 | 8/2004 | Mulier et al. |
| 6,270,497 | B1 | 8/2001 | Sekino et al. | 6,790,217 | B2 | 9/2004 | Schulze et al. |
| 6,270,508 | B1 | 8/2001 | Klieman et al. | 6,796,981 | B2 | 9/2004 | Wham et al. |
| 6,273,887 | B1 | 8/2001 | Yamauchi et al. | D496,997 | S | 10/2004 | Dycus et al. |
| 6,277,117 | B1 | 8/2001 | Tetzlaff et al. | 6,802,843 | B2 | 10/2004 | Truckai et al. |
| 6,280,458 | B1 | 8/2001 | Boche et al. | 6,808,525 | B2 | 10/2004 | Latterell et al. |
| 6,283,961 | B1 | 9/2001 | Underwood et al. | D499,181 | S | 11/2004 | Dycus et al. |
| D449,886 | S | 10/2001 | Tetzlaff et al. | 6,818,000 | B2 | 11/2004 | Muller et al. |
| 6,302,424 | B1 | 10/2001 | Gisinger et al. | 6,887,240 | B1 | 5/2005 | Lands et al. |
| 6,319,451 | B1 | 11/2001 | Brune | 6,926,716 | B2 | 8/2005 | Baker et al. |
| 6,322,561 | B1 | 11/2001 | Eggers et al. | 6,929,644 | B2 | 8/2005 | Truckai et al. |
| 6,334,860 | B1 | 1/2002 | Dorn | 6,932,810 | B2 | 8/2005 | Ryan |
| 6,334,861 | B1 | 1/2002 | Chandler et al. | 6,932,816 | B2 | 8/2005 | Phan |
| 6,345,532 | B1 | 2/2002 | Coudray et al. | 6,934,134 | B2 | 8/2005 | Mori et al. |
| 6,350,264 | B1 | 2/2002 | Hooven | 6,936,061 | B2 | 8/2005 | Sasaki |
| 6,352,536 | B1 | 3/2002 | Buysse et al. | 6,942,662 | B2 | 9/2005 | Goble et al. |
| 6,358,249 | B1 | 3/2002 | Chen et al. | 6,953,461 | B2 | 10/2005 | McClurken et al. |
| 6,358,268 | B1 | 3/2002 | Hunt et al. | 6,958,070 | B2 | 10/2005 | Witt et al. |
| D457,958 | S | 5/2002 | Dycus et al. | 6,960,210 | B2 | 11/2005 | Lands et al. |
| D457,959 | S | 5/2002 | Tetzlaff et al. | 6,964,662 | B2 | 11/2005 | Kidooka |
| 6,387,094 | B1 | 5/2002 | Eitenmuller | 6,966,907 | B2 | 11/2005 | Goble |
| 6,391,035 | B1 | 5/2002 | Appleby et al. | 6,977,495 | B2 | 12/2005 | Donofrio |
| 6,398,779 | B1 | 6/2002 | Buysse et al. | 6,979,786 | B2 | 12/2005 | Aukland et al. |
| 6,402,747 | B1 | 6/2002 | Lindemann et al. | 6,994,707 | B2 | 2/2006 | Ellman et al. |
| 6,409,728 | B1 | 6/2002 | Ehr et al. | 6,994,709 | B2 | 2/2006 | Iida |
| H2037 | H | 7/2002 | Yates et al. | 7,011,657 | B2 | 3/2006 | Truckai et al. |
| 6,419,675 | B1 | 7/2002 | Gallo, Sr. | 7,033,354 | B2 | 4/2006 | Keppel |
| 6,425,896 | B1 | 7/2002 | Baltschun et al. | 7,033,356 | B2 | 4/2006 | Latterell et al. |
| 6,443,952 | B1 | 9/2002 | Mulier et al. | 7,041,102 | B2 | 5/2006 | Truckai et al. |
| 6,443,970 | B1 | 9/2002 | Schulze et al. | 7,044,948 | B2 | 5/2006 | Keppel |
| 6,451,018 | B1 | 9/2002 | Lands et al. | 7,052,496 | B2 | 5/2006 | Yamauchi |
| 6,458,125 | B1 | 10/2002 | Cosmescu | D525,361 | S | 7/2006 | Hushka |
| 6,458,128 | B1 | 10/2002 | Schulze | 7,070,597 | B2 | 7/2006 | Truckai et al. |
| 6,458,130 | B1 | 10/2002 | Frazier et al. | 7,083,618 | B2 | 8/2006 | Couture et al. |
| 6,464,701 | B1 | 10/2002 | Hooven et al. | 7,083,619 | B2 | 8/2006 | Truckai et al. |
| 6,464,704 | B2 | 10/2002 | Schmaltz et al. | 7,087,054 | B2 | 8/2006 | Truckai et al. |
| 6,500,176 | B1 | 12/2002 | Truckai et al. | 7,090,673 | B2 | 8/2006 | Dycus et al. |
| 6,503,248 | B1 | 1/2003 | Levine | 7,090,689 | B2 | 8/2006 | Nagase et al. |
| 6,506,189 | B1 | 1/2003 | Rittman, III et al. | 7,101,371 | B2 | 9/2006 | Dycus et al. |
| 6,511,480 | B1 | 1/2003 | Tetzlaff et al. | 7,101,372 | B2 | 9/2006 | Dycus et al. |
| 6,514,251 | B1 | 2/2003 | Ni et al. | 7,101,373 | B2 | 9/2006 | Dycus et al. |
| 6,514,252 | B2 | 2/2003 | Nezhat et al. | 7,103,947 | B2 | 9/2006 | Sartor et al. |
| 6,527,771 | B1 | 3/2003 | Weadock et al. | 7,112,199 | B2 | 9/2006 | Cosmescu |
| 6,544,264 | B2 | 4/2003 | Levine et al. | D531,311 | S | 10/2006 | Guerra et al. |
| 6,558,385 | B1 | 5/2003 | McClurken et al. | 7,115,123 | B2 | 10/2006 | Knowlton et al. |

| Patent No. | Date | Inventor |
|---|---|---|
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,314,471 B2 | 1/2008 | Holman |
| 7,329,256 B2 | 2/2008 | Johnson et al. |
| 7,329,257 B2 | 2/2008 | Kanehira et al. |
| D564,662 S | 3/2008 | Moses et al. |
| 7,342,754 B2 | 3/2008 | Fitzgerald et al. |
| 7,344,268 B2 | 3/2008 | Jigamian |
| 7,367,976 B2 | 5/2008 | Lawes et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0018331 A1 | 1/2003 | Dycus et al. |
| 2003/0069571 A1 | 4/2003 | Treat et al. |
| 2003/0078578 A1 | 4/2003 | Truckai et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158549 A1 | 8/2003 | Swanson |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0236325 A1 | 12/2003 | Bonora |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0078035 A1 | 4/2004 | Kanehira et al. |
| 2004/0116979 A1 | 6/2004 | Truckai et al. |
| 2004/0147925 A1 | 7/2004 | Buysse et al. |
| 2004/0225288 A1 | 11/2004 | Buysse et al. |
| 2004/0230189 A1 | 11/2004 | Keppel |
| 2004/0236325 A1 | 11/2004 | Tetzlaff et al. |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2004/0260281 A1 | 12/2004 | Baxter, III et al. |
| 2005/0004564 A1 | 1/2005 | Wham et al. |
| 2005/0004568 A1 | 1/2005 | Lawes et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0107785 A1 | 5/2005 | Dycus et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0119655 A1 | 6/2005 | Moses et al. |
| 2005/0149017 A1 | 7/2005 | Dycus |
| 2005/0149151 A1 | 7/2005 | Orszulak et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0064085 A1 | 3/2006 | Schechter et al. |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0116675 A1 | 6/2006 | McClurken et al. |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0259036 A1 | 11/2006 | Tetzlaf et al. |
| 2006/0264922 A1 | 11/2006 | Sartor et al. |
| 2006/0264931 A1 | 11/2006 | Chapman et al. |
| 2006/0271038 A1 | 11/2006 | Johnson et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0055231 A1 | 3/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0203485 A1 | 8/2007 | Keppel |
| 2007/0213706 A1 | 9/2007 | Dumbauld et al. |

| | | | | | | |
|---|---|---|---|---|---|---|
| 2007/0213707 | A1 | 9/2007 | Dumbauld et al. | EP | 1707143 A1 | 10/2006 |
| 2007/0213708 | A1 | 9/2007 | Dumbauld et al. | GB | 2214430 A | 6/1989 |
| 2007/0213712 | A1 | 9/2007 | Buysse et al. | GB | 2213416 | 8/1989 |
| 2007/0255279 | A1 | 11/2007 | Buysse et al. | JP | 501068 | 9/1984 |
| 2007/0260235 | A1 | 11/2007 | Podhajsky | JP | 502328 | 3/1992 |
| 2007/0260238 | A1 | 11/2007 | Guerra | JP | 5-5106 | 1/1993 |
| 2007/0260241 | A1 | 11/2007 | Dalla Betta et al. | JP | 5-40112 | 2/1993 |
| 2007/0260242 | A1 | 11/2007 | Dycus et al. | JP | 06343644 A2 | 12/1994 |
| 2007/0265616 | A1 | 11/2007 | Couture et al. | JP | 07265328 A2 | 10/1995 |
| 2008/0004616 | A1 | 1/2008 | Patrick | JP | 08056955 A2 | 3/1996 |
| 2008/0009860 | A1 | 1/2008 | Odom | JP | 08252263 A2 | 10/1996 |
| 2008/0015575 | A1 | 1/2008 | Odom et al. | JP | 09010223 A2 | 1/1997 |
| 2008/0021450 | A1 | 1/2008 | Couture | JP | 11244298 A2 | 9/1999 |
| 2008/0033428 | A1 | 2/2008 | Artale et al. | JP | 2000342599 A2 | 12/2000 |
| 2008/0039835 | A1 | 2/2008 | Johnson et al. | JP | 2000350732 A2 | 12/2000 |
| 2008/0045947 | A1 | 2/2008 | Johnson et al. | JP | 2001008944 A2 | 1/2001 |
| 2008/0058802 | A1 | 3/2008 | Couture et al. | JP | 2001029356 A2 | 2/2001 |
| 2008/0082100 | A1 | 4/2008 | Orton et al. | JP | 2001128990 A2 | 5/2001 |
| | | | | SU | 401367 | 10/1973 |

FOREIGN PATENT DOCUMENTS

| | | | | | |
|---|---|---|---|---|---|
| SU | | 401367 | | 11/1974 | |
| DE | 24 15263 | 10/1975 | WO | WO89/00757 | 1/1989 |
| DE | 2415263 | 10/1975 | WO | WO 92/04873 | 4/1992 |
| DE | 2627679 | 1/1977 | WO | WO 92/06642 | 4/1992 |
| DE | 8712328 | 3/1988 | WO | WO 94/08524 A | 4/1994 |
| DE | 4303882 | 8/1994 | WO | WO94/20025 | 9/1994 |
| DE | 29616210 | 1/1997 | WO | WO 95/02369 | 1/1995 |
| DE | 19608716 | 4/1997 | WO | WO95/07662 | 3/1995 |
| DE | 19751106 | 5/1998 | WO | WO 95/07662 | 3/1995 |
| DE | 19751108 | 5/1999 | WO | WO95/15124 | 6/1995 |
| EP | 0364216 A1 | 4/1990 | WO | WO96/05776 | 2/1996 |
| EP | 0518230 A1 | 12/1992 | WO | WO 96/22056 | 7/1996 |
| EP | 0 541 930 B1 | 5/1993 | WO | WO 96/13218 | 9/1996 |
| EP | 0572131 | 12/1993 | WO | WO 97/00646 | 1/1997 |
| EP | 0572131 A1 | 12/1993 | WO | WO 97/00647 | 1/1997 |
| EP | 0584787 A1 | 3/1994 | WO | WO 97/10764 | 3/1997 |
| EP | 0589453 A2 | 3/1994 | WO | WO97/10764 | 3/1997 |
| EP | 0623316 A1 | 11/1994 | WO | WO 97/24073 | 7/1997 |
| EP | 0624348 A2 | 11/1994 | WO | WO 97/24993 | 7/1997 |
| EP | 0650701 A1 | 5/1995 | WO | WO 98/ 27880 | 7/1998 |
| EP | 0694290 A3 | 3/1996 | WO | WO 99/03407 | 1/1999 |
| EP | 0717966 A1 | 6/1996 | WO | WO 99/03408 | 1/1999 |
| EP | 0754437 A3 | 3/1997 | WO | WO 99/03409 | 1/1999 |
| EP | 0853922 A1 | 7/1998 | WO | WO 99/12488 A | 3/1999 |
| EP | 0875209 A1 | 11/1998 | WO | WO 99/40857 | 8/1999 |
| EP | 0878169 A1 | 11/1998 | WO | WO 99/40861 | 8/1999 |
| EP | 0887046 A3 | 1/1999 | WO | WO 99/51158 | 10/1999 |
| EP | 0923907 A1 | 6/1999 | WO | WO 99/66850 | 12/1999 |
| EP | 0986990 A1 | 3/2000 | WO | WO 99/66850 A | 12/1999 |
| EP | 1034747 A1 | 9/2000 | WO | WO 00/24330 | 5/2000 |
| EP | 1034748 A1 | 9/2000 | WO | WO 00/24331 | 5/2000 |
| EP | 1025807 A3 | 10/2000 | WO | WO00/24331 | 5/2000 |
| EP | 1034746 A3 | 10/2000 | WO | WO 00/41638 | 7/2000 |
| EP | 1050278 A1 | 11/2000 | WO | WO00/47124 | 8/2000 |
| EP | 1053719 A1 | 11/2000 | WO | WO 00/53112 | 9/2000 |
| EP | 1053720 A1 | 11/2000 | WO | WO 01/17448 A | 3/2001 |
| EP | 1055399 A1 | 11/2000 | WO | WO 01/54604 | 8/2001 |
| EP | 1055400 A1 | 11/2000 | WO | WO 01/54604 A1 | 8/2001 |
| EP | 1080694 A1 | 3/2001 | WO | WO02/07627 | 1/2002 |
| EP | 1082944 A1 | 3/2001 | WO | WO 02/07627 | 1/2002 |
| EP | 1159926 A2 | 12/2001 | WO | WO 02/067798 A1 | 9/2002 |
| EP | 1301135 A | 4/2003 | WO | WO 02/080783 | 10/2002 |
| EP | 1330991 A1 | 7/2003 | WO | WO02/080783 | 10/2002 |
| EP | 1486177 A2 | 6/2004 | WO | WO 02/080784 | 10/2002 |
| EP | 1472984 A1 | 11/2004 | WO | WO02/080784 | 10/2002 |
| EP | 1527747 A2 | 5/2005 | WO | WO 02/080785 | 10/2002 |
| EP | 1530952 A1 | 5/2005 | WO | WO02/080785 | 10/2002 |
| EP | 1532932 A1 | 5/2005 | WO | WO02/080786 | 10/2002 |
| EP | 1535581 A2 | 6/2005 | WO | WO 02/080786 | 10/2002 |
| EP | 1609430 A1 | 12/2005 | WO | WO 02/080793 | 10/2002 |
| EP | 1632192 A1 | 3/2006 | WO | WO02/080793 | 10/2002 |
| EP | 1645238 A2 | 4/2006 | WO | WO 02/080794 | 10/2002 |
| EP | 1645240 A2 | 4/2006 | WO | WO02/080794 | 10/2002 |
| | | | WO | WO 02/080795 | 10/2002 |

| | | |
|---|---|---|
| WO | WO 02/080796 | 10/2002 |
| WO | WO 02/080796 A1 | 10/2002 |
| WO | WO02/080797 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO02/081170 | 10/2002 |
| WO | WO 03/090630 A3 | 11/2003 |
| WO | WO 03/101311 | 12/2003 |
| WO | WO 2004/032776 A1 | 4/2004 |
| WO | WO 2004/032777 | 4/2004 |
| WO | WO2004/032777 | 4/2004 |
| WO | WO 2004/052221 A1 | 6/2004 |
| WO | WO 2004/073488 A2 | 9/2004 |
| WO | WO2004/073490 | 9/2004 |
| WO | WO 2004/073490 | 9/2004 |
| WO | WO2004/073753 | 9/2004 |
| WO | WO 2004/082495 | 9/2004 |
| WO | WO 2004/082495 A1 | 9/2004 |
| WO | WO2004/098383 A1 | 11/2004 |
| WO | WO 2004/103156 | 12/2004 |
| WO | WO2005/004735 | 1/2005 |
| WO | WP 2005/004734 A1 | 1/2005 |
| WO | WO 2005/110264 | 11/2005 |

OTHER PUBLICATIONS

Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended- EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Olsson et al. "Radical Cystectomy in Females" Current Surgical Techniques in Urology, vol. 14, Issue 3, 2001.
Dulemba et al. "Use of a Bipolar Electrothermal Vessel Sealer in Laparoscopically Assisted Vaginal Hysterectomy" Sales Product Literature; Jan. 2004.
Johnson et al. "Evaluation of a Bipolar electrothermal Vessel Sealing Device in Hemorrhoidectomy" Sales Product Literature; Jan. 2004.
International Search Report PCT/US01/11224 dated Nov. 13, 2001.
International Search Report EP 98958575.7 dated Sep. 20, 2002.
International Search Report EP 04013772 dated Apr. 1, 2005.
International Search Report EP 05013895 dated Oct. 14, 2005.
International Search Report EP 05017281 dated Nov. 16, 2005.
PCT/US01/11340, International Search Report.
PCT/US01/11420, International Search Report.
PCT/US02/01890, International Search Report.
PCT/US02/11100, International Search Report.
PCT/US04/03436, International Search Report.
PCT/US04/13273, International Search Report.
PCT/US04/15311, International Search Report.
EP 98944778, International Search Report.
EP 98958575, International Search Report.
EP 04027479, International Search Report.
EP 04027705, International Search Report.
EP 04027314, International Search Report.
"Innovations in Electrosurgery" Sales/Product Literature.
LigaSure Vessel Sealing System, the Seal of Confidence in General, Gynecologic, Urologic, and Laparaoscopic Surgery Sales/Product Literature.
Carbonell et al., "Comparison of theGyrus PlasmaKinetic Sealer and the Valleylab LigaSure Device in the Hemostasis of Small, Medium, and Large-Sized Ateries" Carolinas Laparoscopic and Advanced Surgery Program, Carolinas Medical Center, Charlotte, NC.
"Reducing Needlestick injuries in the Operating Room" Sales/Product Literature.
Chung et al., "Clinical Experience of Sutureless Closed Hemorrhoidectomy with LigaSure" Diseases of the Colon & Rectum vol. 46, No. 1 Jan. 2003.
Strasberg et al., "Use of a Bipolar Vessel-Sealing Device for Parenchymal Transection During Liver Surgery" Journal of Gastrointestinal Surgery, vol. 6, No. 4, Jul./Aug. 2002, pp. 569-574.
Paul G. Horgan, "A Novel Technique for Parenchymal Division During Hepatectomy" The American Journal of Surgery, vol. 181, No. 3, Apr. 2001 pp. 236-237.
W. Scott Helton, "LigaSure Vessel Sealing System: Revolutionary Hemostasis Product for General Surgery" Sales/Product Literature.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealin System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al., "Laparoscopic Intestinal Resection With the LigaSure Vessel Sealing System: A Case Report" Innovations That Work, Feb. 2002.
Carus et al., "Initial Experience With The LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing For Hemostasis During Gynecologic Surgery" Sales Product Literature.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3.
E. David Crawford "Use of a Novel Vessel Sealing Technology in Management of the Dorsal Veinous Complex" Sales Product Literature.
Jarrett et al., "Use of the LigaSure Vessel Sealing System for Peri-Hilar Vessels in Laparoscopic Nephrectomy" Sales Product Literature.
E. David Crawford "Evaluation of a New Vessel Sealing Device in Urologic Cancer Surgery" Sales Product Literature.
Joseph Ortenberg "LigaSure System Used in Laparoscopic 1st and 2nd Stage Orchiopexy" Innovations That Work, Nov. 2002.
Koyle et al., "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales Product Literature.
Johnson et al., "Evaluation of a Bipolar electrothermal Vessel Sealing Device in Hemorrhoidectomy" Sales Product Literature.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the UgaSure Vessel Sealing System in Hepatic Surgery" Section of HPB Surger, Washington University School of Medicine, St. Louis MO, Presented at AHPBA, Feb. 2001.

Johnson et al. "Evaluation of the LigaSure Vessel Sealing System in Hemorrhoidectomy" American College of Surgeons (ACS) Clinicla Congress Poster (2000).

Sayfan et al. "Sutureless Closed Hemorrhoidectomy: A New Technique" Annals of Surgery vol. 234 No. 1 Jul. 2001 pp. 21-24.

Heniford et al. "Initial Results with an Electrothermal Bipolar Vessel Sealer" Surgical Endoscopy (2000) 15:799-801.

Heniford et al. "Initial Research and Clinical Results with an Electrothermal Bipolar Vessel Sealer" Oct. 1999.

McLellan et al. "Vessel Sealing for Hemostasis During Pelvic Surgery" Int'l Federation of Gynecology and Obstetrics FIGO World Congress 2000, Washington, D.C.

Levy et al. "Use of a New Energy-based Vessel Ligation Device During Vaginal Hysterectomy" Int'l Federation of Gynecology and Obstetrics (FIGO) World Congress.

Crawford et al. "Use of the LigaSure Vessel Sealing System in Urologic Cancer Surger" Grand Rounds in Urology 1999 vol. 1 Issue 4 pp. 10-17.

Rothenberg et al. "Use of the LigaSure Vessel Sealing System in Minimally Invasive Surgery in Children" Int'l Pediatric Endosurgery Group (IPEG) 2000.

Palazzo et al. "Randomized clinical trial of Ligasure versus open haemorrhoidectomy" British Journal of Surgery 2002, 89, 154-157.

Int'l Search Report PCT/US01/11218.
Int'l Search Report PCT/US99/24869.
Int'l Search Report PCT/US98/18640.
Int'l Search Report PCT/US98/23950.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 04013772 dated Apr. 1, 2005.
Int'l Search Report EP 05013895 dated Oct. 14, 2005.
Int'l Search Report EP 05017281 dated Nov. 16, 2005.
Int'l Search Report EP 06006716 dated Aug. 4, 2006.
Int'l Search Report PCT/US01/11224 dated Nov. 13, 2001.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.
Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 01 4016 dated Jan. 28, 2008.
Int'l Search Report EP 07 020283.3 dated Jan. 16, 2008.
Int'l Search Report EP 05 019429.9 dated Apr. 11, 2008.
US 6,090,109, 07/2000, Lands et al. (withdrawn)
US 6,663,629, 12/2003, Buysse et al. (withdrawn)

VESSEL SEALING INSTRUMENT

CROSS REFERENCE TO RELATED APPLICATIONS

This application claims the benefit of and priority to International Application No. PCT/US01/11420 filed on Apr. 6, 2001 which is a continuation-in-part of U.S. application Ser. No. 09/425,696 filed Oct. 22, 1999 by Philip Mark Tetzlaff et al., now U.S. Pat. No. 6,511,480, which is a continuation-in-part of U.S. application Ser. No. 09/178,027 filed Oct. 23, 1998 by Philip Mark Tetzlaff et al., now U.S. Pat. No. 6,277,117, the entire contents of each of these applications are hereby incorporated by reference.

BACKGROUND

The present disclosure relates to forceps used for open surgical procedures. More particularly, the present disclosure relates to a forceps which applies a combination of mechanical clamping pressure and electrosurgical current to seal tissue.

Technical Field

A hemostat or forceps is a simple plier-like tool which uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

Certain surgical procedures require sealing and cutting blood vessels or vascular tissue. Several journal articles have disclosed methods for sealing small blood vessels using electrosurgery. An article entitled *Studies on Coagulation and the Development of an Automatic Computerized Bipolar Coagulator*, J. Neurosurg., Volume 75, July 1991, describes a bipolar coagulator which is used to seal small blood vessels. The article states that it is not possible to safely coagulate arteries with a diameter larger than 2 to 2.5 mm. A second article is entitled *Automatically Controlled Bipolar Electrocoagulation—"COA-COMP"*, Neurosurg. Rev. (1984), pp. 187-190, describes a method for terminating electrosurgical power to the vessel so that charring of the vessel walls can be avoided.

By utilizing an electrosurgical forceps, a surgeon can either cauterize, coagulate/desiccate, reduce or slow bleeding and/or seal vessels by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is typically attached externally to the patient. When the electrosurgical energy is applied, the energy travels from the active electrode, to the surgical site, through the patient and to the return electrode.

Bipolar electrosurgical forceps utilize two generally opposing electrodes which are disposed on the inner opposing surfaces of the end effectors and which are both electrically coupled to an electrosurgical generator. Each electrode is charged to a different electric potential. Since tissue is a conductor of electrical energy, when the effectors are utilized to grasp tissue therebetween, the electrical energy can be selectively transferred through the tissue.

In order to effect a proper seal with larger vessels, two predominant mechanical parameters must be accurately controlled—the pressure applied to the vessel and the gap between the electrodes both of which affect thickness of the sealed vessel. More particularly, accurate application of the pressure is important to oppose the walls of the vessel, to reduce the tissue impedance to a low enough value that allows enough electrosurgical energy through the tissue, to overcome the forces of expansion during tissue heating and to contribute to the end tissue thickness which is an indication of a good seal. It has been determined that a fused vessel wall is optimum between 0.001 and 0.005 inches. Below this range, the seal may shred or tear and above this range the lumens may not be properly or effectively sealed.

With respect to smaller vessel, the pressure applied to the tissue tends to become less relevant whereas the gap distance between the electrically conductive surfaces becomes more significant for effective sealing. In other words, the chances of the two electrically conductive surfaces touching during activation increases as the vessels become smaller.

Electrosurgical methods may be able to seal larger vessels using an appropriate electrosurgical power curve, coupled with an instrument capable of applying a large closure force to the vessel walls. It is thought that the process of coagulating small vessels is fundamentally different than electrosurgical vessel sealing. For the purposes herein, "coagulation" is defined as a process of desiccating tissue wherein the tissue cells are ruptured and dried and vessel sealing is defined as the process of liquefying the collagen in the tissue so that it reforms into a fused mass. Thus, coagulation of small vessels is sufficient to permanently close them. Larger vessels need to be sealed to assure permanent closure.

Numerous bipolar electrosurgical forceps have been proposed in the past for various open surgical procedures. However, some of these designs may not provide uniformly reproducible pressure to the blood vessel and may result in an ineffective or non-uniform seal. For example, U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, cutting and/or sealing vessels or tissue.

Many of these instruments include blade members or shearing members which simply cut tissue in a mechanical and/or electromechanical manner and are relatively ineffective for vessel sealing purposes. Other instruments rely on clamping pressure alone to procure proper sealing thickness and are not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, a thicker less reliable seal is created.

As mentioned above, in order to properly and effectively seal larger vessels, a greater closure force between opposing jaw members is required. It is known that a large closure force between the jaws typically requires a large moment about the pivot for each jaw. This presents a challenge because the jaw members are typically affixed with pins which are positioned to have a small moment arms with respect to the pivot of each jaw member. A large force, coupled with a small moment arm, is undesirable because the large forces may shear the pins. As a result, designers must compensate for these large closure forces by either designing instruments with metal pins and/or by designing instruments which at least partially offload these closure forces to reduce the chances of mechanical failure. As can be appreciated, if metal pivot pins are employed, the metal pins must be insulated to avoid the pin acting as an alternate current path between the jaw members which. may prove detrimental to effective sealing.

Increasing the closure forces between electrodes may have other undesirable effects, e.g., it may cause the opposing electrodes to come into close contact with one another which may result in a short circuit and a small closure force may cause pre-mature movement of the issue during compression and prior to activation.

Thus, a need exists to develop a bipolar forceps which effectively seals vascular tissue and solves the aforementioned problems by providing an instrument which enables a large closure force between the opposing jaws members, reduces the chances of short circuiting the opposing jaws during activation and assists in manipulating, gripping and holding the tissue prior to and during activation.

SUMMARY

The present disclosure relates to a bipolar electrosurgical instrument for use in open surgery which includes first and second shafts one of which is connectable to a source of electrosurgical energy. Each shaft includes a jaw member extending from a distal end thereof and a handle disposed at a proximal end thereof for effecting movement of the jaw members relative to one another from a first, open position wherein the jaw members are disposed in spaced relation relative to one another to a second, closed position wherein the jaw members cooperate to grasp tissue therebetween. The source of electrical energy effects first and second electrical potentials in the respective jaw members such that the jaw members are capable of selectively conducting energy through tissue held therebetween to effect a seal.

Preferably, the first and second electrical potentials are created at the jaw members through the first shaft. For example, in one embodiment, the first electrical potential is transmitted through the first shaft by a lead having a terminal end which electrically interfaces with a distal connector which connects a first jaw member to the first electrical potential. The second electrical potential is transmitted through the first shaft by a tube disposed within the first shaft which connects the second jaw member to the second electrical potential.

The first and second jaw members are connected about a pivot pin. The distal connector is preferably interposed between the jaw members and includes a series of flanges which are dimensioned to prevent the emanation of stray currents from the electrically conductive sealing surfaces of the jaw members during activation.

Preferably, the distal connector includes a spring washer or wave washer which acts as an electrical intermediary between the terminal end and the jaw member. In one embodiment, the spring washer is beveled to enhance the electrical interface between the terminal end and the jaw member, i.e., beveling causes the spring washer to rotate relative the terminal end during movement of the jaw members from the first to second positions which provides a self-cleaning, enhanced running electrical contact between the terminal end and the jaw member.

Preferably, the distal connector is made from an insulative substrate and is disposed between the jaw members for electrically isolating the first and second potentials. In one embodiment, the distal connector includes a first surface having at least one recess defined therein which is dimensioned to receive at least a portion of the terminal end of the lead.

In yet another embodiment, one of the jaw members includes a skirt which is dimensioned to prevent exposure of the terminal end during all angles of operation, i.e., when the jaw members are disposed in the first position, the second position and/or during operative movement therebetween.

The lead preferably includes a inner core made from a solid or multi-strand electrically conductive material, e.g., copper/aluminum wire, which is surrounded by an insulative, non-conductive coating, e.g., plastic. In one embodiment, the terminal or distal end of the electrically conductive material is flattened, i.e., "flat-formed", and is dimensioned to substantially encircle a boss which extends from the surface of the distal connector. Preferably, the boss is designed to electrically insulate the terminal end of the lead from the pivot pin.

In another embodiment, at least one non-conductive stop member is disposed on an electrically conductive sealing surface of one of the jaw members. The stop members are designed to control/regulate the distance, i.e., gap, between the jaw members when tissue is held therebetween during activation

BRIEF DESCRIPTION OF THE DRAWINGS

Various embodiments of the subject instrument are described herein with reference to the drawings wherein.

DETAILED DESCRIPTION

Figure 1:
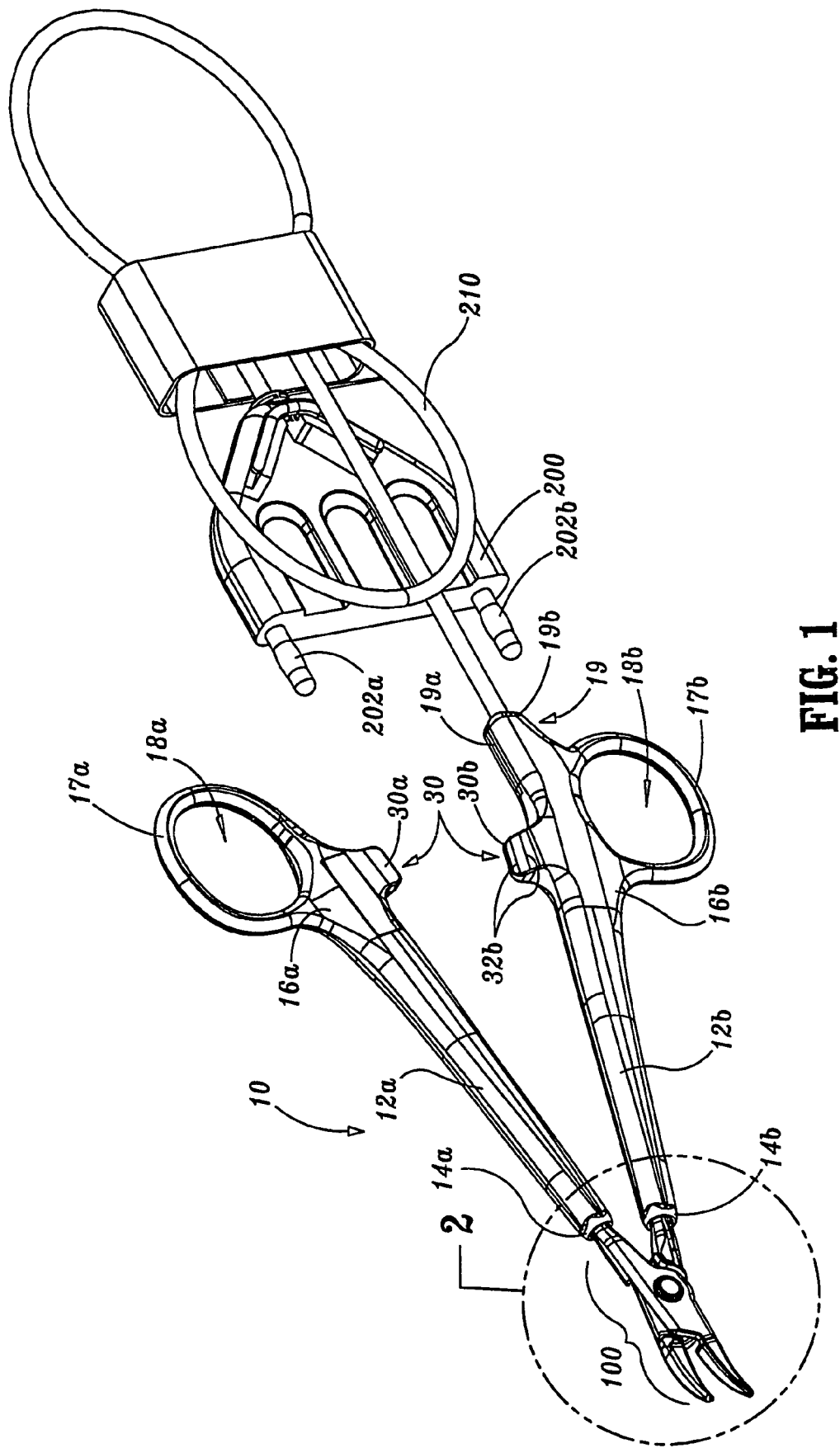
FIG. 1 is a left, perspective view of a forceps according to the present disclosure.
Figure 2:
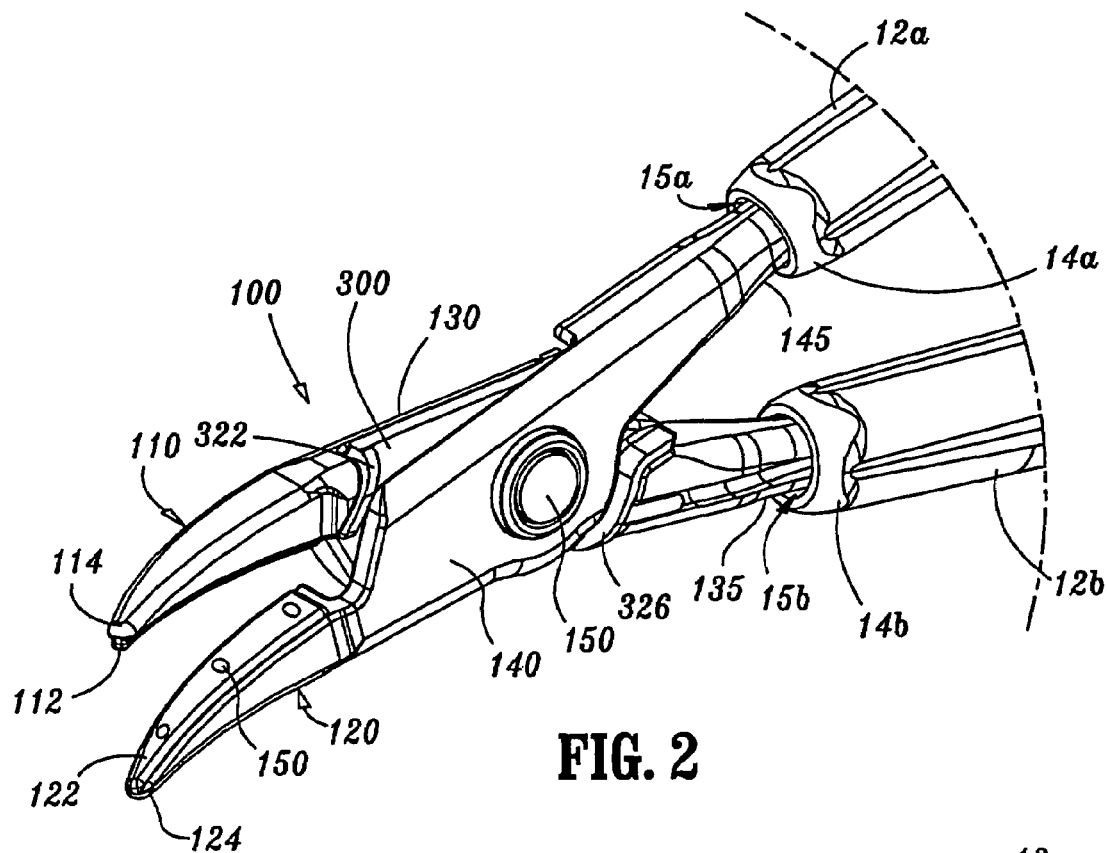
FIG. 2 is an enlarged, perspective view of an end effector assembly of the forceps of FIG. 1 shown in open configuration.
Figure 3:
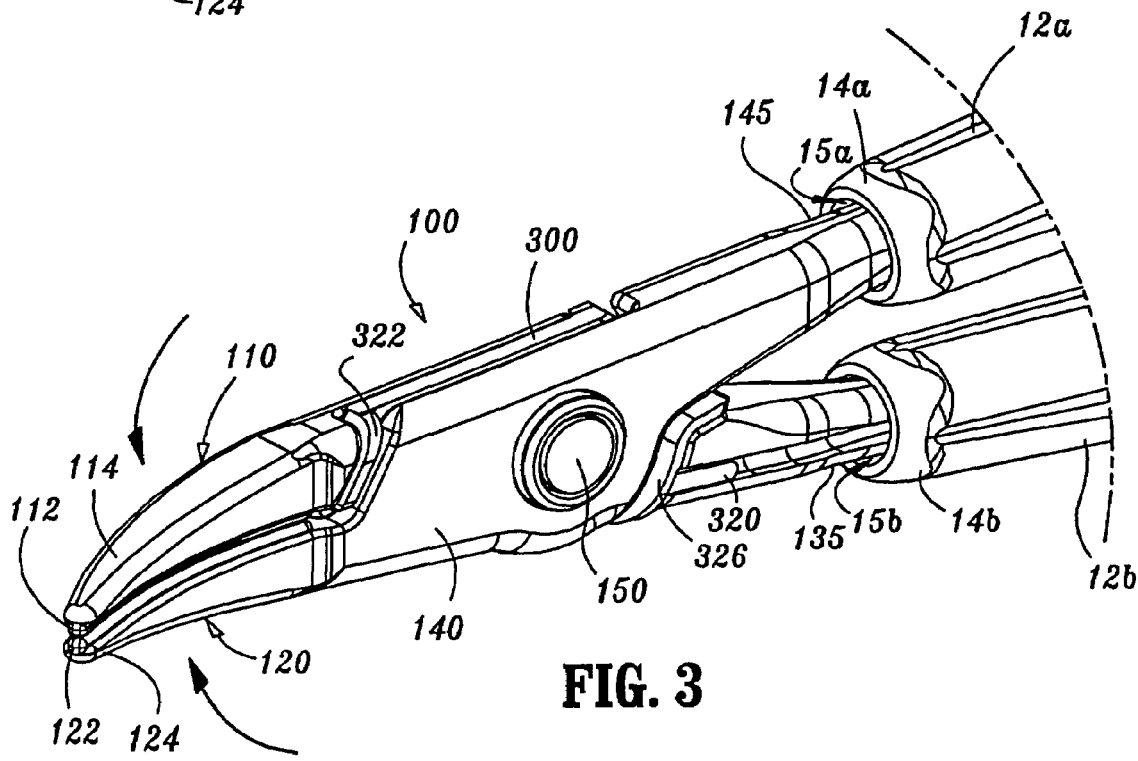
FIG. 3 is an enlarged, perspective view of the end effector assembly of the forceps of FIG. 1 shown in closed configuration.

Referring now to FIGS. 1-4, a forceps 10 for use with open surgical procedures includes elongated shaft portions 12*a* and 12*b* each having a proximal end 16*a* and 16*b*, respectively, and a distal end 14*a* and 14*b*, respectively. In the drawings and in the descriptions which follow, the term "proximal", as is traditional, will refer to the end of the forceps 10 which is closer to the user, while the term "distal" will refer to the end which is further from the user.

The forceps 10 includes an end effector assembly 100 which attaches to distal ends 14a and 14b of shafts 12a and 12b, respectively. As explained in more detail below, the end effector assembly 100 includes pair of opposing jaw members 110 and 120 which are pivotably connected about a pivot pin 151.

Preferably, each shaft 12a and 12b includes a handle 17a and 17b disposed at the proximal end 16a and 16b thereof which each define a finger hole 18a and 18b, respectively, therethrough for receiving a finger of the user. As can be appreciated, finger holes 18a and 18b facilitate movement of the shafts 12a and 12b relative to one another which, in turn, pivot the jaw members 110 and 120 from an open position (FIG. 2) wherein the jaw members 110 and 120 are disposed in spaced relation relative to one another to a clamping or closed position (FIG. 3) wherein the jaw members 110 and 120 cooperate to grasp tissue 400 (FIG. 6) therebetween.

Figure 6:
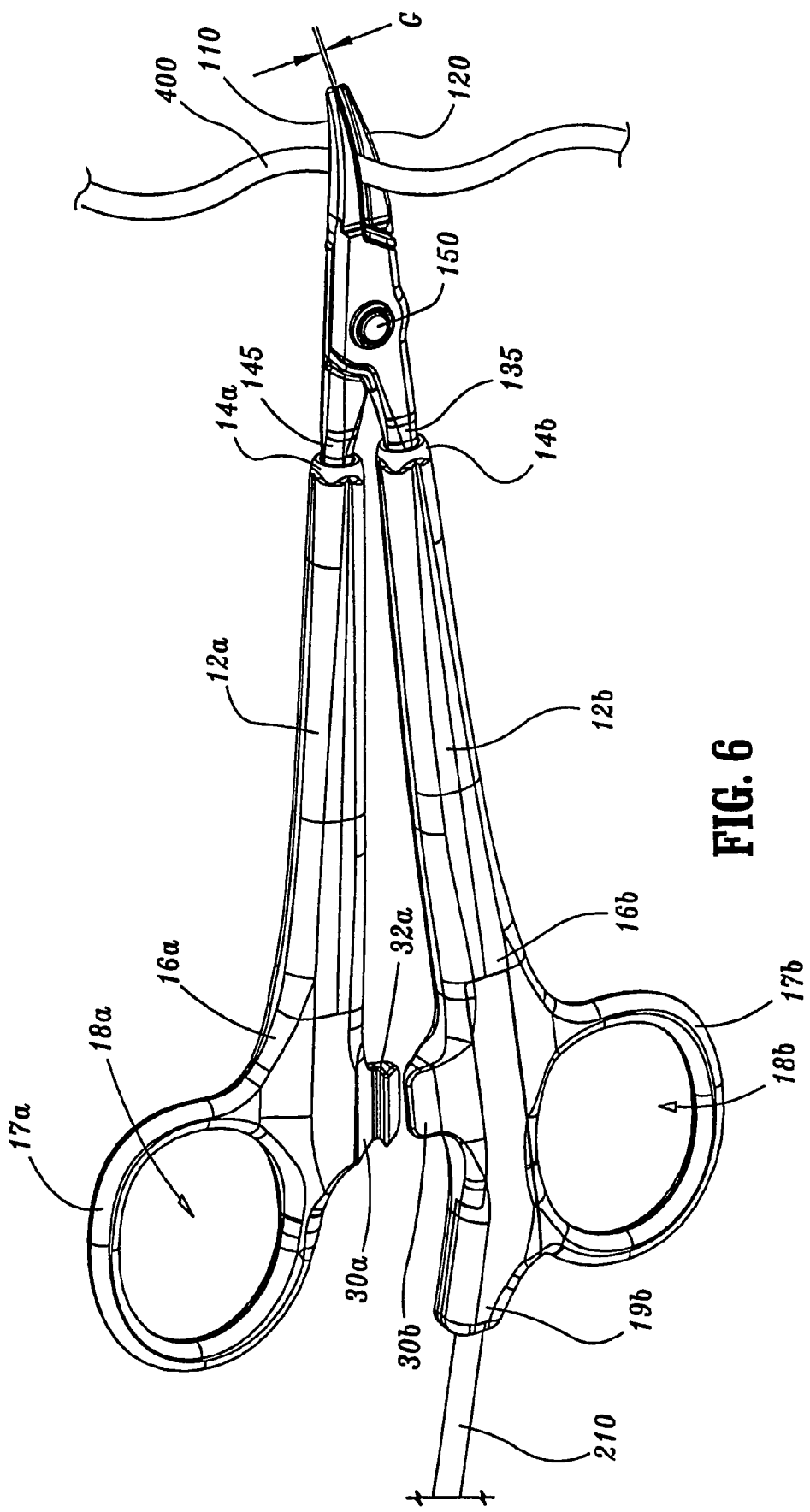
FIG. 6 is a right, perspective view of the forceps of FIG. 1 shown grasping a tissue structure.

A ratchet 30 is preferably included for selectively locking the jaw members 110 and 120 relative to one another at various positions during pivoting. As best shown in FIG. 6, a first ratchet interface, e.g., 30a, extends from the proximal end 16a of shaft member 12a towards a second ratchet interface 30b in a generally vertically aligned manner such that the inner facing surfaces of each ratchet 30a and 30b abut one another upon closure about the tissue 400. Preferably, each ratchet interface 30a and 30b includes a plurality of flanges 32a and 32b, respectively, which projects from the inner facing surface of each ratchet interface 30a and 30b such that the ratchet interfaces 30a and 30b interlock in at least one position. In the embodiment shown in FIG. 6, the ratchet interfaces 30a and 30b interlock at several different positions.

Preferably, each position associated with the cooperating ratchet interfaces 30a and 30b holds a specific, i.e., constant, strain energy in the shaft members 12a and 12b which, in turn, transmits a specific closing force to the jaw members 110 and 120. It is envisioned that the ratchet 30 may include graduations or other visual markings Which enable the user to easily and quickly ascertain and control the amount of closure force desired between the jaw members. A design without a ratchet system or similar system would require the user to hold the jaw members 110 and 120 together by applying constant force to the handles 17a and 17b which may yield inconsistent results.

As best illustrated in FIG. 1, one of the shafts, e.g., 12b, includes a proximal shaft connector 19 which is designed to connect the forceps 10 to a source of electrosurgical energy such as an electrosurgical generator (not shown). More particularly, proximal shaft connector 19 is formed by a cover 19a and a flange 19b which extends proximally from shaft 12b. Preferably, cover 19a and flange 19b mechanically cooperate to secure an electrosurgical cable 210 to the forceps 10 such that the user may selectively apply electrosurgical energy as needed.

The proximal end of the cable 210 includes a plug 200 having a pair of prongs 202a and 202b which are dimensioned to electrically and mechanically engage the electrosurgical energy generator. As explained in more detail below with respect to FIG. 8, the distal end of the cable 210 is secured to the proximal shaft connector 19 of shaft 12b by a plurality of finger-like clamping members 77a and 77b and a cable crimp having opposing fingers 76a and 76b. The interior of cable 210 houses a pair of leads 210a and 210b which conduct the different electrical potentials from the electrosurgical generator to the jaw members 110 and 120 as explained in greater detail below.

As best seen in FIGS. 2-4B, the two opposing jaw members 110 and 120 of the end effector assembly 100 are pivotable about pin 151 from the open position to the closed position for grasping tissue 400 therebetween. Jaw members 110 and 120 are generally symmetrical and include similar component features which cooperate to permit facile rotation about pivot pin 151 to effect the grasping and sealing of tissue 400. As a result and unless otherwise noted, jaw member 110 and the operative features associated therewith will initially be described herein in detail and the similar component features with respect to jaw member 120 will be briefly summarized thereafter.

Jaw member 110 includes an insulated outer housing 114 which is dimensioned to mechanically engage an electrically conductive sealing surface 112 and a proximally extending flange 130 which is dimensioned to seat a distal connector 300 which is described in more detail below with respect to FIGS. 4A, 4B and 5. Preferably, outer insulative housing 114 extends along the entire length of jaw member 110 to reduce alternate or stray current paths during sealing and/or incidental burning of tissue 400. The inner facing surface of flange 130 includes an electrically conductive plate 134 (FIG. 4B) which conducts electrosurgical energy to the electrically conductive sealing surface 112 upon activation.

Likewise, jaw member 120 include similar elements which include: an outer housing 124 which engages an electrically conductive sealing surface 122; a proximally extending flange 140 which seats the opposite face of the distal connector 300; an electrically conductive plate 144 which conducts electrosurgical energy to the electrically conductive sealing surface 122 upon activation.

It is envisioned that one of the jaw members, e.g., 110, includes at least one stop member 150 disposed on the inner facing surface of the electrically conductive sealing surface 112 (and/or 122). The stop member(s) is preferably designed to facilitate gripping and manipulation of tissue 400 and to define a gap "G" (FIG. 6) between opposing jaw members 110 and 120 during sealing. A detailed discussion of these and other envisioned stop members 150 as well as various manufacturing and assembling processes for attaching, disposing, depositing and/or affixing the stop members 150 to the electrically conductive sealing surfaces 112, 122 are described in commonly-assigned, co-pending PCT Application Ser. No. PCT/US01/11222 entitled "BIPOLAR ELECTROSURGICAL FORCEPS WITH NON-CONDUCTIVE STOP MEMBERS" which is hereby incorporated by reference in its entirety herein.

Figure 4A:
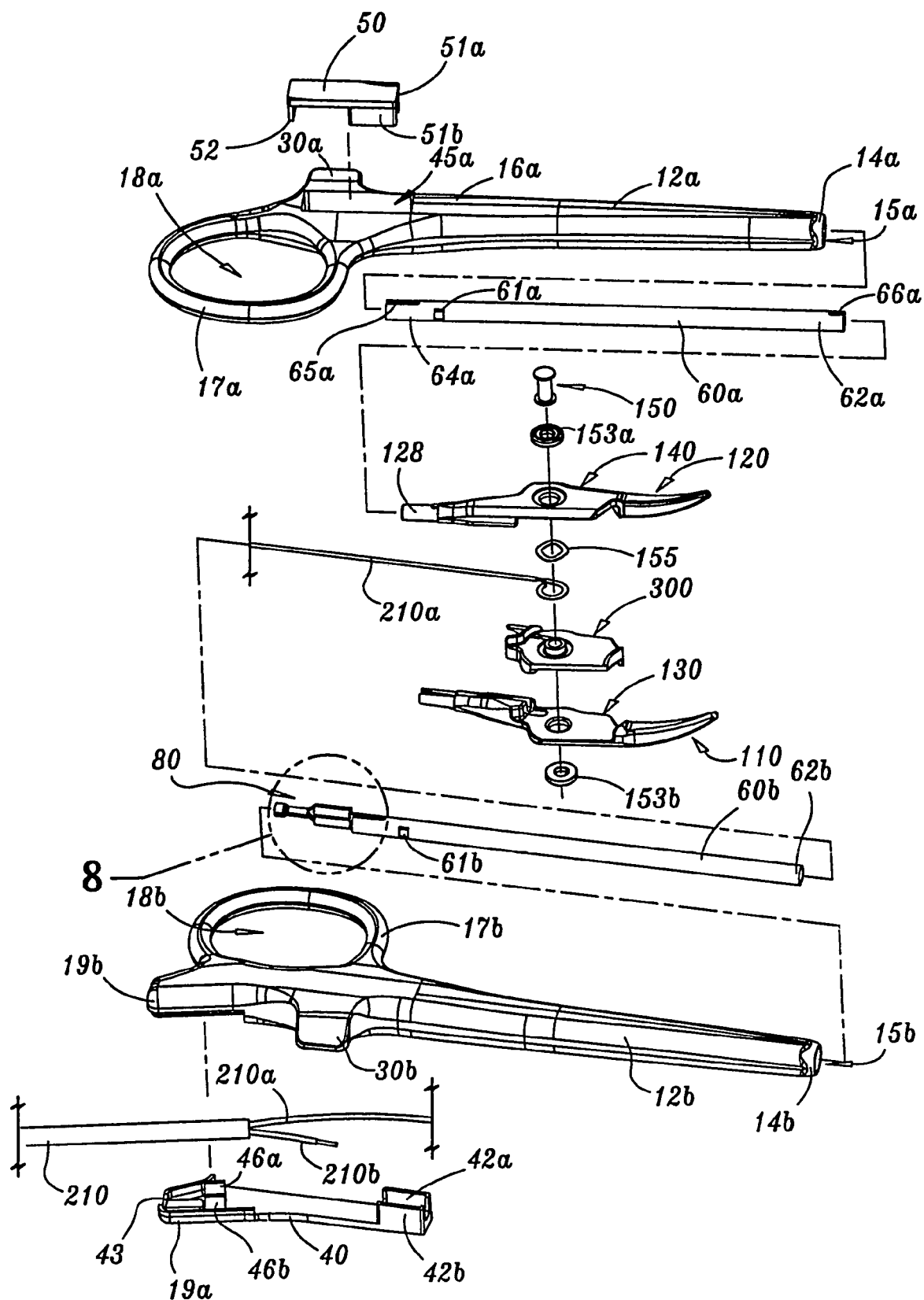
FIG. 4A is an exploded view of the forceps according to the present disclosure.
Figure 5:
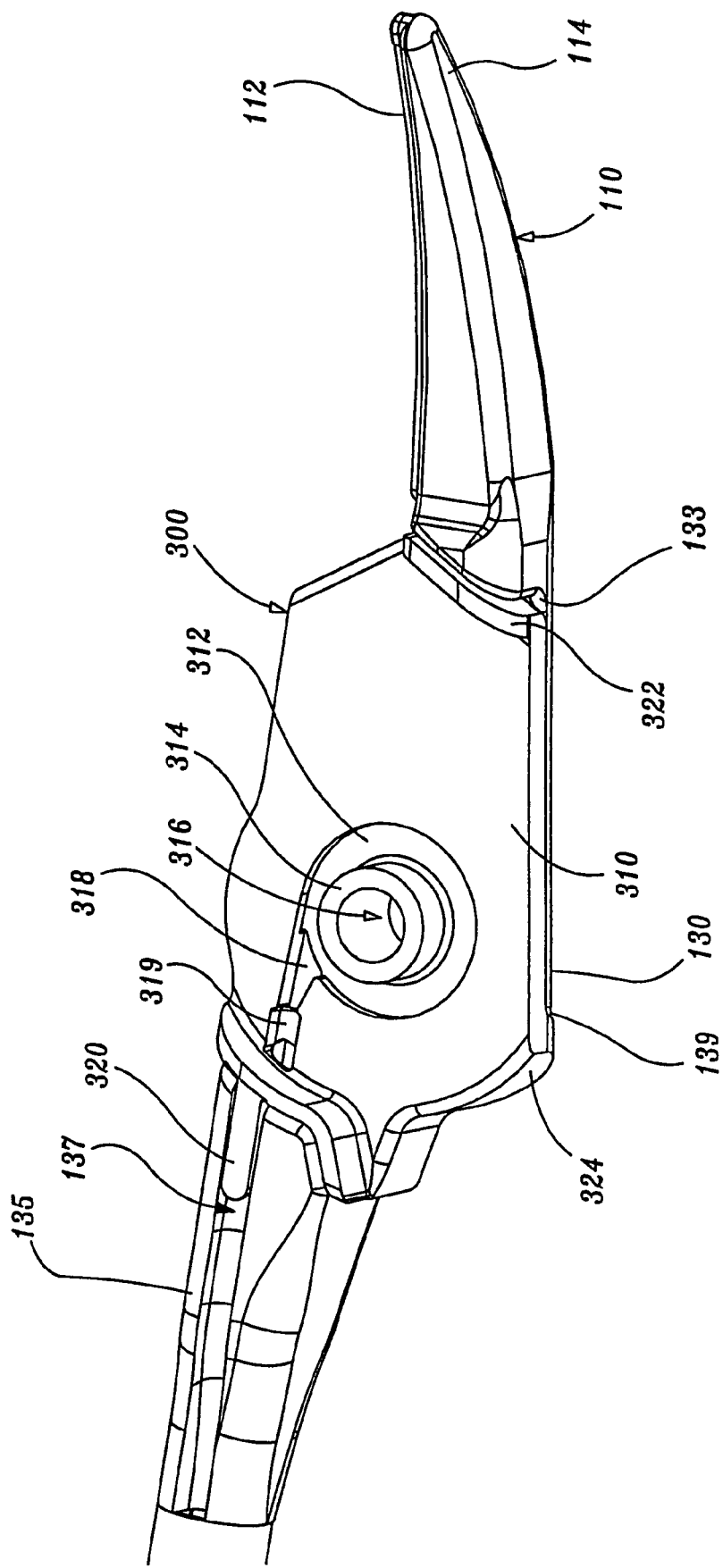
FIG. 5 is an enlarged, top perspective view of a lower jaw member of forceps with the distal connector seated thereon.

FIG. 4A shows an exploded view of the various components of the forceps 10 and the inter-operative relationships among the same. More particularly and in addition to the components described above with respect to FIGS. 1-3 above, shaft 12a is preferably hollow to define a longitudinal channel 15a disposed therethrough which is dimensioned to receive a tube 60a therein. Tube 60a includes a proximal end 64a, a distal end 62a and at least one mechanical interface 61a disposed therebetween. Shaft 12a also includes a cover plate 50 which is designed for snap-fit engagement within an aperture/cavity 45a defined through the outer surface of shaft 12a. Cover plate 50 includes a series of opposing flanges 51a and 51b which extend therefrom which are dimensioned to secure the tube 60a within shaft 12a as described below. A second flange 52 secures the cover plate 50 to the shaft 12a.

During assembly, the proximal end 64a of tube 60a is slideable incorporated within channel 15a such that mechanical interface 61a is poised for engagement with cover plate 50. Cover plate 50 is then snapped into cavity 45a such that flanges 51a and 51b secure tube 60a within shaft 12a. It is envisioned that the cavity 45a of shaft 12a may include at least one detent (not shown) which engages mechanical interface 61a disposed along the outer surface of tube 60a to limit/prevent rotation of the tube 60a relative to the shaft 12a. This cooperative relationship is shown by way of example with respect to. detents 75a and 75b and interfaces (e.g., notches) 61b of shaft 12b in FIG. 8. In this instance, flanges 51a and 51b (much like flanges 42a and 42b of cover plate 40 in FIG. 8) hold the detents 75a and 75b in FIG. 8) in secure engagement within the notch(es) 61a to prevent rotational and/or longitudinal movement of the tube 60a within the channel 15a.

Preferably, the proximal-most end of tube 60a includes a slit-like interface 65a which mechanically engages a corresponding tongue 88a extending from the inner surface of shaft 12a within cavity 45a. It is envisioned that tongue 88a also prevents rotational movement of the tube 60a within the shaft 12a. Alternatively, slit 65a may be formed to allow radial contraction and expansion of the tube 60a to promote friction-fit engagement between the tube 60a and the shaft 12a. Other interfaces are also envisioned which will facilitate engagement of the shaft 12a and the tube 60a, e.g., snap-fit, spring-lock, locking tabs, screw-like interface, tongue and groove, etc.

The distal end 62a of tube 60a is preferably dimensioned to engage jaw member 120, i.e., the distal end 62a includes a slit-like interface 66a which promotes simple, secure friction-fit engagement of the tube 60a with the jaw member 120. More particularly and as mentioned above, jaw member 120 includes a proximally extending flange 130 having a sleeve 128 extending proximally therefrom which is dimensioned such that, upon insertion of the sleeve 128 within distal end 62a, slit-like interface 66a expands radially outwardly and securely locks the jaw member 120 to tube 60a. Again, other methods of attachment are also envisioned which would serve the same purpose, e.g., snap-locks, locking tabs, spring-locks, screw-like interface, tongue and groove, etc.

Figure 4B:
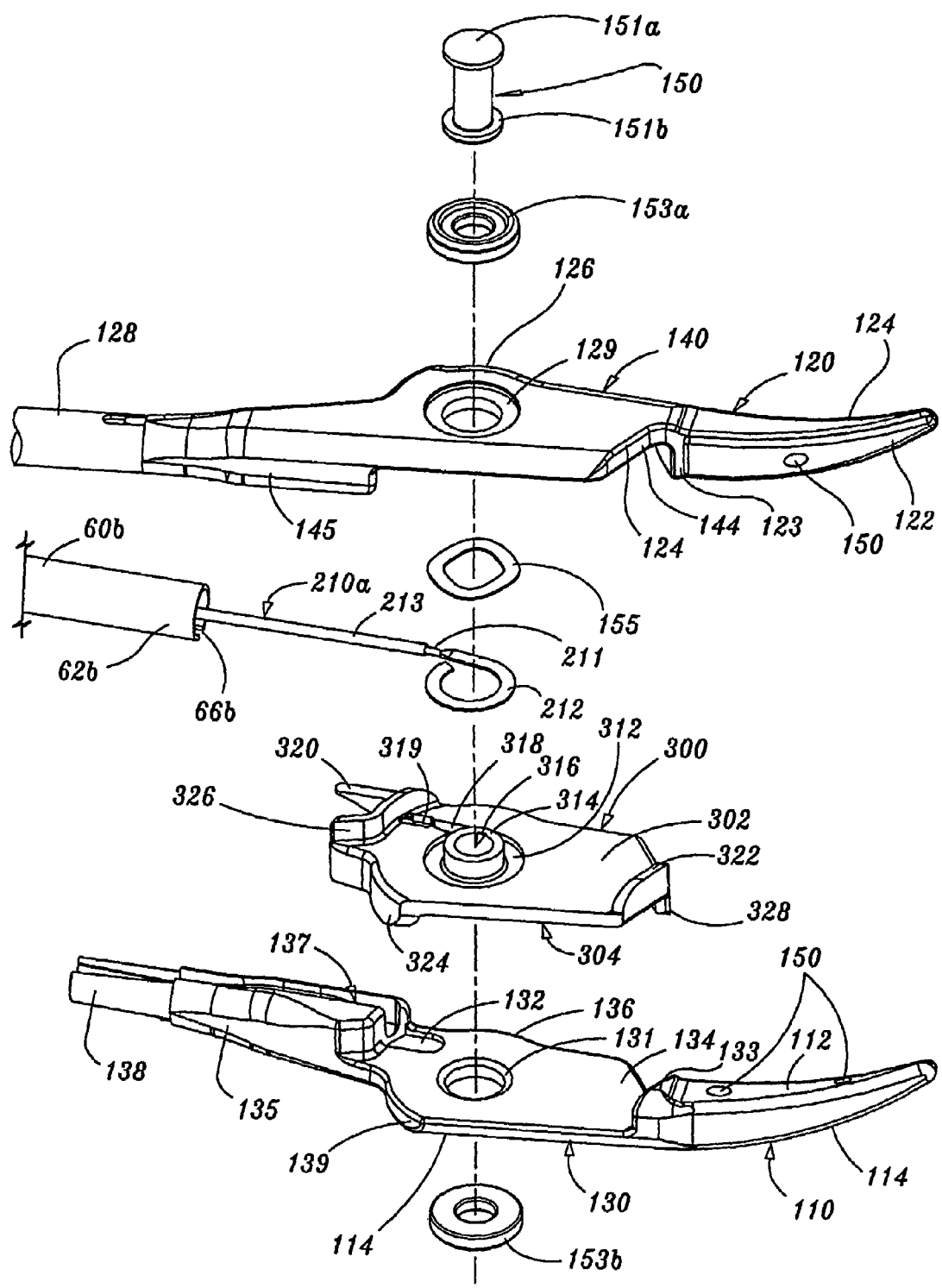
FIG. 4B is an enlarged, exploded view of the end effector assembly of FIG. 4A showing the electrical connection of a distal electrical connector for supplying electrical energy to the end effector assembly.
Figure 7:
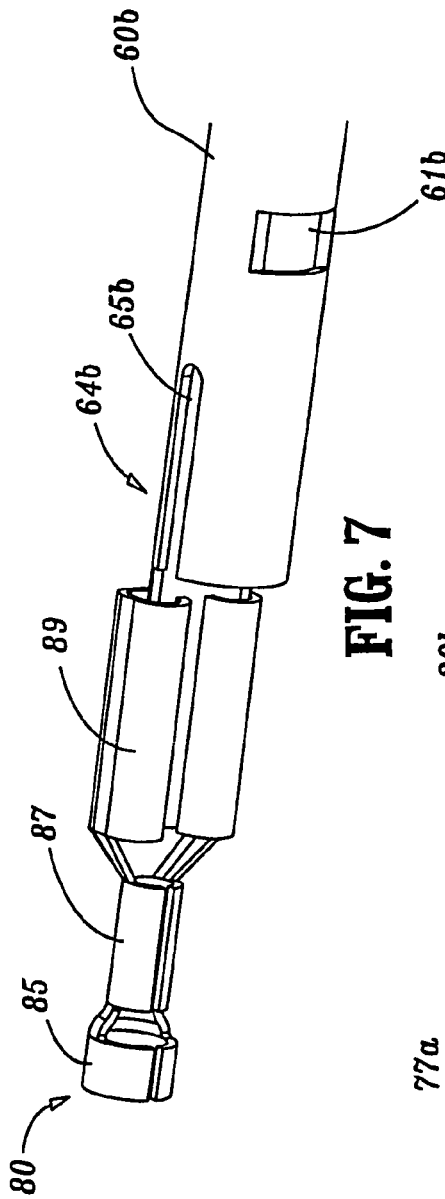
FIG. 7 is a enlarged view of the indicated area of detail in FIG. 4A showing a proximal electrical interface/connector for supplying electrical energy to the end effector assembly.
Figure 8:
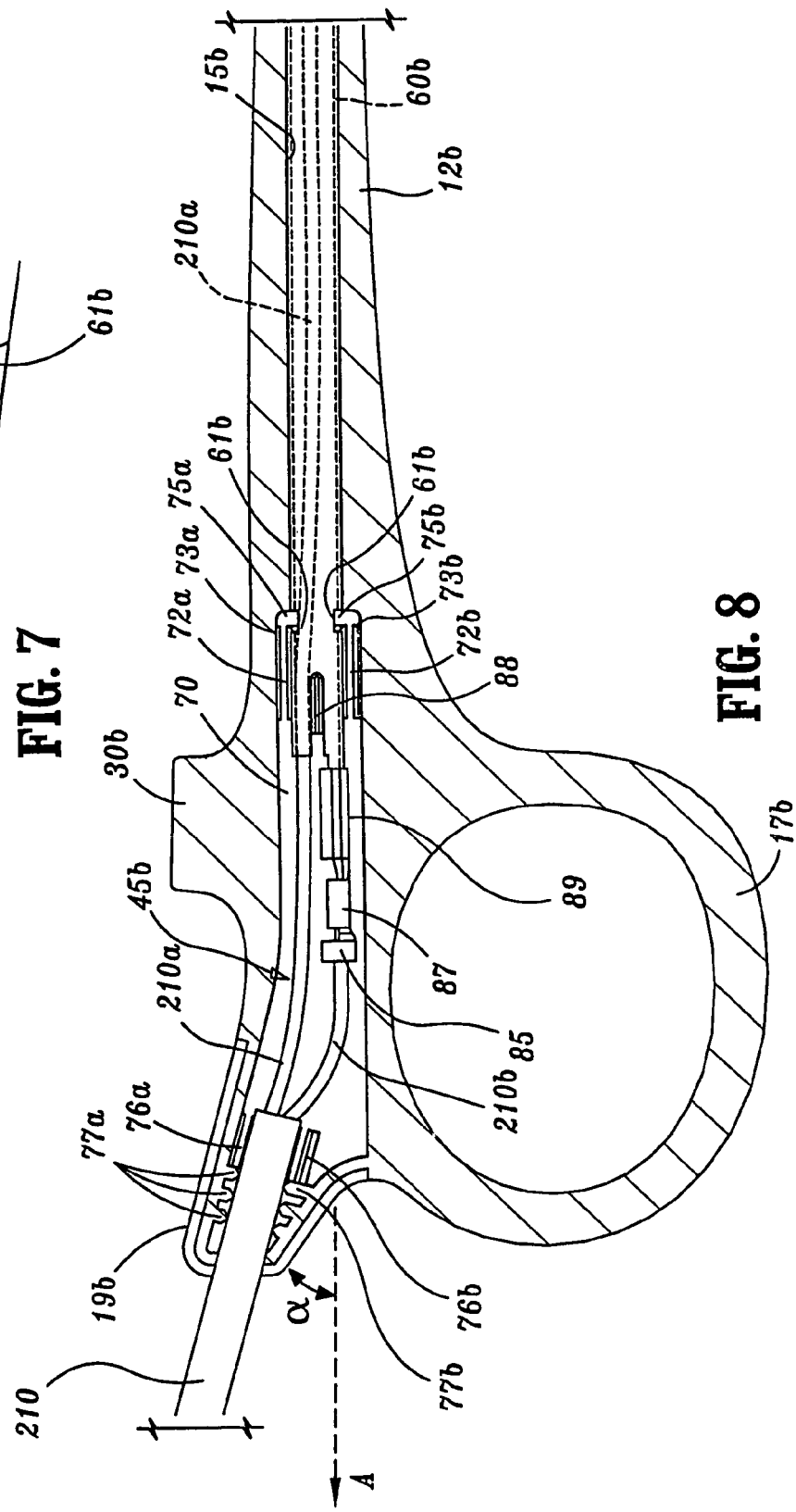
FIG. 8 is a cross section of the forceps of FIG. 6 showing the electrical feed path of a first lead having a first electrical potential and showing the electrical connection of the proximal electrical interface of FIG. 7 with a second lead having a second electrical potential.

As can be appreciated by the present disclosure, the arrangement of shaft 12b is slightly different from shaft 12a as shown best in FIGS. 4B, 7 and 8. More particularly, shaft 12b is also hollow to define a channel 15b therethrough and is dimensioned to receive a tube 60b therein. Tube 60b includes a proximal end 64b and a distal end 62b which attach in a generally similar fashion as their counterpart components with respect to shaft 12a. For example, the proximal end 64b of tube 60b is slideable incorporated within channel 15b such that a mechanical interface 61b disposed on the outer surface of tube 60b is poised for engagement with a cover plate 40 (FIGS. 4A and 8).

Preferably and since the forceps 10 is uniquely designed to incorporate all of the electrical interfaces and connections within and along a single shaft, e.g., 12b, shaft 12b includes a slightly larger cavity 45b defined therein for housing and securing the various electrical connections associated with the forceps 10 as described below. For example, cover plate 40 is dimensioned slightly differently than cover plate 50 mostly due to the spatial considerations which must be taken into account for incorporation of the various internally disposed electrical connections. However, cover plate 40 does snap atop shaft 12b such that a pair of flanges 42a and 42b secure tube 60b within shaft 12b in a similar manner as described above. For example, FIG. 8 shows a pair of detents 75a and 75b disposed within the cavity 45b of shaft 12b which engage a corresponding number of mechanical interfaces 61b disposed along the outer surface of tube 60b to limit/prevent rotation of the tube 60b relative to the shaft 12b. When assembled, each flange 42a and 42b is pushed into a corresponding groove 73a and 73b, respectively, which effectively maintain/hold the detents 75a and 75b in secure engagement within the notches 61b to prevent rotational and/or longitudinal movement of the tube 60b within the channel 15b.

End 64b of tube 60b also includes a slit-like interface 65b which mechanically engages a corresponding tongue 88b extending from the inner surface of shaft 12b within cavity 45b. It is envisioned that tongue 88a also prevents rotational movement of the tube 60b within the shaft 12b. Alternatively, slit 65b may be formed to allow radial contraction and expansion of the tube 60b to promote friction-fit engagement between the tube 60b and the shaft 12b.

Unlike tube 60a, tube 60b is designed as an electrical conduit for transmitting electrosurgical energy to jaw member 110 which is explained In more detail below with respect to FIGS. 7 and 8. The distal end 62b of tube 60b is preferably dimensioned to engage jaw member 110, i.e., the distal end 62b includes a slit-like interface 66b which promotes simple, secure friction-fit engagement of the tube 60b with the jaw member 110. This is best illustrated in FIG. 4B which shows proximally extending flange 130 of jaw member 110 having a terminal sleeve 138 which extends therefrom. Terminal sleeve 138 is dimensioned such that, upon insertion of the terminal sleeve 138 within distal end 62b, slit-like interface 66b expands radially outwardly and securely locks the jaw member 110 to tube 60b.

As can be appreciated, terminal end 138 is at least partially made from an electrically conductive material such that an electrosurgical potential is effectively conducted from the tube 60b, through the terminal sleeve 138, across plate 134 and to the electrically conductive sealing plate 112 upon activation. As mentioned above, the outer insulative housing 114 of jaw member 110 effectively eliminates stray electrical currents and incidental burning of tissue across the intended electrical path.

As best shown in FIG. 4B, jaw member 110 includes a raceway 135 extending proximally from the flange 130 which includes terminal sleeve 138 at the proximal-most end thereof. The terminal sleeve 138 connects to the conductive tube 60b disposed within shaft 12b as described above. Raceway 135 serves two purposes: 1) to provide electrical continuity from the terminal sleeve 138, through the electrically conductive plate 134 and to the electrically conductive sealing surface 112; and 2) to provide a channel for guiding lead 210a to the distal connector 300 as described below.

Insulated outer housing 114 is dimensioned to securely engage the electrically conductive sealing surface 112. It is envisioned that this may be accomplished by stamping, by overmolding, by overmolding a stamped electrically conductive sealing plate and/or by overmolding a metal injection molded seal plate. All of these manufacturing techniques produce an electrode having an electrically conductive surface 112 which is substantially surrounded by an insulated outer housing 114.

It is envisioned that the jaw member may also include a second insulator (not shown) disposed between the electrically conductive sealing surface 112 and the outer insulative housing 114. The insulated outer housing 114 and the electrically conductive sealing surface 112 (and the other insulator if utilized) are preferably dimensioned to limit and/or reduce many of the known undesirable effects related to tissue sealing, e.g., flashover, thermal spread and stray current dissipation.

It is also envisioned that the electrically conductive sealing surface 112 may include a pinch trim (not shown) which facilitates secure engagement of the electrically conductive surface 112 to the insulated outer housing 114 and also simplifies the overall manufacturing process. It is also contemplated that the electrically conductive sealing surface 112 may include an outer peripheral edge which has a radius and the insulated outer housing 114 meets the electrically conductive sealing surface 112 along an adjoining edge which is generally tangential to the radius and/or meets along the radius. Preferably, at the interface, the electrically conductive surface 112 is raised relative to the insulated outer housing 114. These and other envisioned embodiments are discussed in concurrently-filed, co-pending, commonly assigned PCT Application Ser. No. PCT/US01/11412 entitled "ELECTROSURGICAL INSTRUMENT WHICH REDUCES COLLATERAL DAMAGE TO ADJACENT TISSUE" by Johnson et al. and concurrently-filed, co-pending, commonly assigned PCT Application Ser. No. PCT/US01/11411 entitled "ELECTROSURGICAL INSTRUMENT WHICH IS DESIGNED TO REDUCE THE INCIDENCE OF FLASHOVER" by Johnson et al.

As best illustrated in the exploded view of FIG. 4B, the inner periphery of tube 60b is preferably dimensioned to house lead 210a therethrough such that a different electrically potential can be effectively transmitted to jaw member 120. More particularly and as mentioned above, cable 210 houses two leads 210a and 210b having different electrical potentials. The first lead 210a is disposed through tube 60b and conducts the first electrical potential to jaw member 120 as described in more detail below. The second lead 210b is electrically interfaced with tube 60b at a proximal connector 80 (FIG. 7) which includes a series of electrical crimps 85, 87 and 89 for securing lead 210b to tube 60b. As a result, tube 60b carries the second electrical potential therethrough for ultimate connection to jaw member 110 as described above.

Lead 210a preferably includes an insulative coating 213 which surrounds an inner core or electrical conductor 211 (e.g., wire) disposed therein to insulate the electrical conductor 211 from the tube 60b during activation. It is envisioned that the wire 211 may be made from a solid or multi-strand electrically conductive material, e.g., copper/aluminum, which is surrounded by an insulative, non-conductive coating 213, e.g., plastic.

The wire 211 includes a terminal end 212 which is dimensioned to electrically interface with jaw member 120. Preferably, the terminal end 212 is "flat-formed" in a generally arcuate shape to encircle a corresponding boss 314 which extends upwardly from the distal connector 300 towards jaw member 120 as described below. It is envisioned that the distal connector 300 performs at least two functions: 1) to insulate jaw member 110 from jaw member 120; and 2) to provide a running electrical connection for lead 210a to jaw member 120.

More particularly, the distal connector 300 is generally shaped to match the overall profile of the electrically conductive face plates 134 and 144 of jaw members 110 and 120, respectively, such that, upon assembly, outer facing surfaces 302 and 304 of the distal connector 300 abut against the corresponding plates 134 and 144 of jaw member 110 and 120, respectively. It is envisioned that the outer facing surface 302 of the distal connector 300 acts as a runway surface which facilitates pivotable motion of jaw member 120 about pivot pin 151 relative to jaw member 110. Preferably, the distal connector 300 is made form an insulative substrate such as plastic or some other non-conductive material.

The distal connector includes a series of flanges 322 and 326 which extend towards jaw member 120 and a second series of flanges 324 and 328 which extend towards jaw member 110. It is envisioned that these flanges 322, 324, 326 and 328 insulate the other operative components of the forceps 10 and the patient from stray electrical currents emanating from the electrically conductive plates 134 and 144 during activation. Flanges 322 and 328 may also be dimensioned to limit/restrict the expansion of tissue 400 beyond the sealing surfaces 112 and 122 during activation. Flanges 326 and 324 are preferably dimensioned to insulate the forceps during all angles of operation, i.e., pivoting of the jaw members 110 and 120.

As mentioned above, the distal connector 300 includes a boss 314 which extends towards jaw member 120 which is dimensioned to secure the terminal end 212 of lead 210a. Preferably, the boss is designed to electrically insulate the terminal end of the lead from the pivot. The boss 314 preferably defines an aperture 316 therethrough for receiving the pivot pin 151 and to allow pivotable motion of jaw member 120 about the pivot 151 and the boss 314 relative to jaw member 110.

A continuous series of recesses 312, 318 and 319 are formed around and proximate boss 314 to seat the flat-formed terminal end 212, the wire 211 and the insulated portion of the lead 210a, respectively. This also secures lead 210a to the distal connector and limits movement of the same (210a). In some cases it may be preferable to include a dollop of silicone or other non-conductive material at the junction between the wire and the terminal end 212 as an added and/or alternative insulating safeguard. It is also envisioned that flange 326 may include a notch (not shown) disposed therethrough which facilitates assembly of the lead 210a atop the distal connector 300. As can be appreciated, this eliminates the step of forming the arcuately-shaped terminal end 212 after insertion through channel 318. As mentioned above, a dollop of silicone or the like may be added atop/within the notch for insulation purposes after the terminal end 212 is seated within the distal connector 300.

The proximal-most portion of distal connector 300 includes a finger 320 which is dimensioned to seat within a channel 137 formed within the raceway 135 such that the distal connector 300 moves in connection with jaw member 110 during pivoting. Channel 137 may be formed during a molding process, subsequently bored after the raceway 135 is formed or by any other known method of formation. The uppermost edge of boss 314 is preferably dimensioned to seat within a corresponding recess (not shown) formed within plate 144. Likewise and although not shown, it is envisioned that the opposite end of boss 314 extends towards plate 134 and seats within a recess 131 formed within plate 134. It is envisioned that recess 131 promotes engagement of the distal connector 300 with the jaw member 110.

The distal connector 300 also includes a spring washer or wave washer 155 which is preferably dimensioned to encircle the boss 314 atop terminal end 212. Upon assembly, the washer 155 is sandwiched/wedged between the terminal end 212 and the conductive plate 144 of jaw member 120. It is envisioned that the washer 155 enhances the connection between the terminal end 212 and the plate 144. More particularly, the washer 155 is preferably shaped such that the washer 155 provides a self-cleaning, running electrical contact between the terminal end 212 and the jaw member 120. It is contemplated that the washer 155 "self-cleans" due to the frictional contact and relative movement of the washer 155 with respect to the terminal end 212 during pivoting of the jaw members 110 and 120. The self-cleaning action can be attributed to the washer 155 rubbing, scoring and/or digging against the terminal end 212 and/or the plate 144 during pivoting of the jaw members 110 and 120.

The outer housing of each of the jaw members 110 and 120 preferably includes an additional recess or circular groove 129 which receives a ring-like insulator 153*b* and 153*a*, respectively. Insulators 153*a* and 153*b* insulate the pivot pin 151 from the jaw members 110 and 120 when the forceps 10 is assembled. Preferably, the pivot pin 151 is peened to secure the jaw members 110 and 120 during assembly and may include outer rims 151*a* and 151*b* at least one of which is peened or formed after the jaw members 110 and 120 are assembled about the pivot pin 151 as best shown in FIG. 4B.

Upon activation, the first electrical potential is carried by lead 210*a* through tube 60*b* to the terminal end 212. The washer 155 of the distal connector 300 then conducts the first potential to face plate 144 which carries the first potential to sealing plate 122 disposed on the inner facing surface of jaw member 120. The second potential is carried by lead 210*b* which electrically interfaces with the tube 60*b* (by way of crimps 85, 87 and 89) to conduct the second potential to terminal sleeve 138 of jaw member 110. The terminal sleeve 138 electrically connects to sealing surface 112 across face plate 134.

FIG. 8 shows the connection of the cable 210 within the cavity 45*b* of shaft 12*b*. As mentioned above a series of finger-like elements 77*a* and 77*b* and crimps 76*a* and 76*b* secure the cable 210 within shaft 12*b*. Preferably, cable 210 is secured at an angle alpha (α) relative to a longitudinal axis "A" disposed along shaft 12*b*. It is envisioned that angling the cable 210 in an inward direction, i.e., towards shaft 12*a*, facilitates handling of the forceps 10 and the cable 210 during surgery, i.e., the angled disposition of the cable 210 as it exits the forceps 10 tends to reduce cable tangling and/or cable interference during handling.

Preferably at least one of the jaw members 110 and 120 includes a skirt-like feature 126 and 136, respectively, which is dimensioned to prevent exposure of the terminal end 212 or wire 211 during all angles of operation, i.e., when the jaw members 110 and 120 are disposed in the first open position, the second closed position and/or during operative movement therebetween.

It is envisioned that by making the forceps 10 disposable, the forceps 10 is less likely to become damaged since it is only intended for a single use and, therefore, does not require cleaning or sterilization. As a result, the functionality and consistency of the vital sealing components, e.g., the conductive surfaces 112 and 122, the stop member(s) 150, and the insulative housings 124 and 114 will assure a uniform and quality seal.

From the foregoing and with reference to the various figure drawings, those skilled in the art will appreciate that certain modifications can also be made to the present disclosure without departing from the scope of the present disclosure. For example, it may be preferable to include a tang which facilitates manipulation of the forceps 10 during surgery.

Moreover, although the electrical connections are preferably incorporated with the bottom shaft 12*b* and the instrument is intended for right-handed use, it is contemplated the electrical connections may be incorporated with the other shaft 12*a* depending upon a particular purpose and/or to facilitate manipulation by a left-handed user.

It is also contemplate that a shrink tube may be employed over the proximal connector 80 and/or the other various solder or crimp connections 85, 87 and 89 associated with the proximal connector 80 interface with lead wire 210*b*. This provides additional insulating protection during assembly. It is also contemplated that the forceps 10 (and/or the electrosurgical generator used in connection with the forceps 10) may include a sensor or feedback mechanism (not shown) which automatically selects the appropriate amount of electrosurgical energy to effectively seal the particularly-sized tissue 400 grasped between the jaw members 110 and 120. The sensor or feedback mechanism may also measure the impedance across the tissue during sealing and provide an indicator (visual and/or audible) that an effective seal has been created between the jaw members 110 and 120.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplications of a preferred embodiments. Those skilled in the art will envision other modifications within the scope and spirit of the claims appended hereto.

What is claimed is:

1. A bipolar electrosurgical instrument for use in open surgery, comprising:

first and second shafts each having a jaw member extending from a distal end thereof and a handle disposed at a proximal end thereof for effecting movement of the jaw members relative to one another from a first position wherein the jaw members are disposed in spaced relation relative to one another to a second position wherein the jaw members cooperate to grasp tissue therebetween, the first jaw member being adapted to connect to a first electrical potential and the second jaw member being adapted to connect to a second electrical potential such that the jaw members are capable of selectively conducting energy through tissue held therebetween to effect a tissue seal;

wherein the first and second electrical potentials are transmitted to the jaw members through the first shaft, the first electrical potential being transmitted by a lead having a terminal end which interfaces with a distal connector to connect one of the jaw members to the first electrical potential; and wherein the distal connector includes a spring washer which acts as an electrical intermediary between the terminal end and the jaw member.

2. A bipolar electrosurgical instrument for use in open surgery according to claim 1, wherein the second electrical potential is transmitted through the first shaft by a tube disposed within the first shaft which connects the other jaw member to the second electrical potential.

3. A bipolar electrosurgical instrument for use in open surgery according to claim 2 wherein the lead is fed to the distal connector through the tube and the lead includes an insulative coating which surrounds a wire-like electrical conductor to insulate the wire-like electrical conductor from the tube during activation.

4. A bipolar electrosurgical instrument for use in open surgery according to claim 1 wherein the spring washer is dimensioned to enhance the electrical interface between the terminal end and the jaw member.

5. A bipolar electrosurgical instrument for use in open surgery according to claim 4 wherein the spring washer is dimensioned to rotate relative the terminal end during movement of the jaw members from the first to second positions to provide a self-cleaning, enhanced electrical contact between the terminal end and the jaw member.

6. A bipolar electrosurgical instrument for use in open surgery according to claim 1 wherein the distal connector is made from an insulative substrate and is interposed between the jaw members for electrically isolating the first and second potentials.

7. A bipolar electrosurgical instrument for use in open surgery according to claim 6 wherein the distal connector includes a first surface having at least one recess defined therein which is dimensioned to receive at least a portion of the terminal end.

8. A bipolar electrosurgical instrument for use in open surgery according to claim 6 wherein at least one of the jaw members includes a skirt which is dimensioned to prevent exposure of the terminal end when the jaw members are disposed in the first position, the second position and during operative movement therebetween.

9. A bipolar electrosurgical instrument for use in open surgery according to claim 1 wherein the terminal end includes a flat-formed wire.

10. A bipolar electrosurgical instrument for use in open surgery according to claim 9 wherein the jaw members are connected by a pivot and the flat-formed wire is dimensioned to substantially encircle a boss extending from the distal connector which receives the pivot.

11. A bipolar electrosurgical instrument for use in open surgery according to claim 1 wherein the jaw members are connected by a pivot and the distal connector includes a boss extending therefrom which is designed to electrically insulate the terminal end from the pivot.

12. A bipolar electrosurgical instrument for use in open surgery, comprising:

first and second shafts each having a jaw member pivotable about a pivot pin and extending from a distal end thereof and a handle disposed at a proximal end thereof for effecting movement of the jaw members relative to one another from a first position wherein the jaw members are disposed in spaced relation relative to one another to a second position wherein the jaw members cooperate to grasp tissue therebetween, each of the jaw members including an electrically conductive sealing surface adapted to connect to an electrical energy source wherein a first electrical potential is connected to one of the jaw members and a second electrical potential is connected to the other of the jaw members such that the jaw members are capable of selectively conducting energy through tissue held therebetween to effect a tissue seal;

the first and second electrical potentials being transmitted to the jaw members through the first shaft wherein the first electrical potential is transmitted by a lead having a terminal end which electrically interfaces with one of the jaw members; and a spring washer disposed between the terminal end and one of the jaw members, the spring washer being dimensioned to rotate relative the terminal end during movement of the jaw members from the first to second positions to provide a self-cleaning, enhanced electrical contact between the terminal end and the jaw member.

13. A bipolar electrosurgical instrument for use in open surgery according to claim 12 wherein the second electrical potential is transmitted through the first shaft by a tube disposed within the first shaft which connects the other jaw member to the second electrical potential.

14. A bipolar electrosurgical instrument for use in open surgery according to claim 12 further comprising an insulator disposed between the jaw members for electrically isolating the first and second potentials.

15. A bipolar electrosurgical instrument for use in open surgery according to claim 12 wherein the terminal end includes a flat-formed wire.

16. A bipolar electrosurgical instrument for use in open surgery according to claim 12 further comprising at least one non-conductive stop member located distally from the pivot pin and operatively associated with at least one of the jaw members to control the distance between the jaw members when tissue is held therebetween.

* * * * *